(12) United States Patent
Nishide et al.

(10) Patent No.: US 7,247,147 B2
(45) Date of Patent: Jul. 24, 2007

(54) MEDICAL BALLOON CATHETER

(75) Inventors: Takuji Nishide, Settsu (JP); Kohei Fukaya, Settsu (JP); Masato Hashiba, Settsu (JP)

(73) Assignee: Kaneka Corporation, Osaka (JP)

( * ) Notice: Subject to any disclaimer, the term of this patent is extended or adjusted under 35 U.S.C. 154(b) by 508 days.

(21) Appl. No.: 10/415,997

(22) PCT Filed: Nov. 8, 2001

(86) PCT No.: PCT/JP01/09773

§ 371 (c)(1),
(2), (4) Date: Jan. 12, 2004

(87) PCT Pub. No.: WO02/38211

PCT Pub. Date: May 16, 2002

(65) Prior Publication Data

US 2004/0116957 A1    Jun. 17, 2004

(30) Foreign Application Priority Data

Nov. 9, 2000  (JP) .............................. 2000-342399
Mar. 2, 2001  (JP) .............................. 2001-059326

(51) Int. Cl.
*A61M 29/00* (2006.01)

(52) U.S. Cl. .............................. 604/103.1; 604/103.04; 604/915

(58) Field of Classification Search ............. 604/96.01, 604/103, 103.04, 523, 915, 917; 606/192, 606/194

See application file for complete search history.

(56) References Cited

U.S. PATENT DOCUMENTS

| | | | | |
|---|---|---|---|---|
| 4,739,768 A | * | 4/1988 | Engelson | 600/435 |
| 5,035,705 A | * | 7/1991 | Burns | 606/194 |
| 5,085,636 A | * | 2/1992 | Burns | 604/99.04 |
| 5,221,260 A | * | 6/1993 | Burns et al. | 604/99.04 |
| 5,423,754 A | * | 6/1995 | Cornelius et al. | 604/103 |
| 5,490,837 A | | 2/1996 | Blaeser et al. | |
| 5,531,689 A | * | 7/1996 | Burns et al. | 604/99.04 |
| 6,113,579 A | * | 9/2000 | Eidenschink et al. | 604/264 |
| 6,231,543 B1 | * | 5/2001 | Hegde et al. | 604/96.01 |
| 6,706,010 B1 | * | 3/2004 | Miki et al. | 604/43 |
| 6,960,186 B1 | * | 11/2005 | Fukaya et al. | 604/103.06 |

FOREIGN PATENT DOCUMENTS

JP       07-132148       5/1995

(Continued)

*Primary Examiner*—Loan H. Thanh
(74) *Attorney, Agent, or Firm*—Hogan & Hartson LLP

(57) ABSTRACT

The medical balloon catheter of the present invention comprises a catheter shaft composed of a distal end shaft and a proximal end shaft and a balloon on the distal end of the distal end shaft, wherein the proximal end shaft is composed of a single member and the distal end portion of the proximal end shaft is lower in rigidity than the other parts thereof. The present invention also provides a medical balloon catheter having a structure in which a tube for passing a guidewire inside thereof is arranged so as to pass inside the balloon and the balloon and tube are fused together in the vicinity of the distal end of the catheter, wherein the ratio of the outer diameter of the small-diameter portion on the distal end side of the tube to the outer diameter of the proximal end portion is no less than 0.85.

6 Claims, 28 Drawing Sheets

FOREIGN PATENT DOCUMENTS

| | | |
|---|---|---|
| JP | 08-289934 | 11/1996 |
| JP | 09-192235 | 7/1997 |
| JP | 11-033122 | 2/1999 |
| JP | 11-151292 | 6/1999 |
| JP | 2000-197704 | 7/2000 |

\* cited by examiner

MEDICAL BALLOON CATHETER

TECHNICAL FIELD

The present invention relates to a medical balloon catheter used for medical applications, and more particularly to a medical balloon catheter for percutaneous angioplasty (PTA: Percutaneous Transluminal Angioplasty, PTCA Percutaneous Transluminal Coronary Angioplasty, and the like) during realization of peripheral angioplasty, coronary angioplasty, valvular angioplasty, and the like.

BACKGROUND ART

Percutaneous angioplasty using medical balloon catheters has been widely used for dilation therapy of stenoses or blocked portions of vascular cavities and for restoration or improvement of blood flow in coronary artery, peripheral blood vessels, and the like. In a typical medical balloon catheter, a balloon that can be inflated or contracted by internal pressure adjustment is joined to the distal end portion of a catheter shaft, and an inner cavity (guidewire lumen) for passing a guidewire and an inner cavity (inflation lumen) for supplying a pressure fluid for internal pressure adjustment in the balloon are provided in the longitudinal direction of the catheter shaft inside thereof.

A typical example of PTCA technique using such a medical balloon catheter is described below. First, a guide catheter is inserted from the punctured zone into a large femoral artery, brachial artery, scapular artery, and the like, and the distal end thereof is disposed in the inlet of a coronary artery via the main artery. The guidewire inserted into the guidewire lumen is then advanced through the stenotic zone, and medical balloon catheter is inserted along the guidewire, and positioned in the stenosis. A pressure fluid is then supplied to the balloon via the inflation lumen by using an indeflator or the like, and dilatotherapy of the stenosis is conducted by inflating the balloon. After the dilatotherapy of the stenosis, PTCA is completed by contracting the balloon by pressure reduction and pulling it out of the body. In the present example of technique, usage of the medical balloon catheter for PTCA in coronary artery stenosis was described, but the medical balloon catheters have been also widely employed for dilatotherapy in body cavities and other vascular cavities such as peripheral vascular cavities.

Such a medical balloon catheter has a structure in which a balloon 2 is joined to the distal end of a catheter shaft 1, and a hub 3 for supplying a pressure fluid for adjusting internal pressure in the balloon is joined to the catheter shaft 1. Based on the structure of catheter shaft 1, the catheters can be classified into two types.

The first type is the over-the-wire type (OTW type) in which the guidewire lumen 4 is provided from the proximal end side to the distal end side of the medical balloon catheter, that is, over the entire length of the medical balloon catheter and a guidewire port is provided in the hub 3 (FIG. 1). The second type is the rapid exchange type (RX type) in which the guidewire lumen is provided on the distal end side of the medical balloon catheter, and the guidewire port 5 is provided in the middle part of catheter shaft 1 (FIG. 2).

A variety of characteristics are required from medical balloon catheters. The main among them can be generally classified into the following three groups: the ability to pass through the stenotic zone (crossability), the ability to follow the curved blood vessel (trackability), and the ability to transmit a force when the medical balloon catheter is inserted into a blood vessel (pushability). Kink resistance is an example of a characteristic relating to pushability.

Reducing the profile (thickness) of catheter shaft improves crossability, but tends to degrade pushability and kink resistance. Further, increasing rigidity of catheter shaft improves pushability and kink resistance, but tends to degrade crossability. In other words, all the above-mentioned characteristics are closely related to each other, and it is not easy to improve all the characteristics at the same time. Accordingly, a variety of techniques for improving crossability, pushability and trackability and increasing kink resistance have been disclosed.

Examined Japanese Patent Application No. 5-28634 (Catheter) discloses a rapid exchange medical balloon catheter, in which an opening of the guidewire lumen is provided in the joining region of a medium portion (distal end shaft in accordance with the present invention) and a base portion (proximal end shaft in accordance with the present invention) and when the guidewire is contained in the guidewire lumen, the catheter receives a continuous longitudinal support over the entire length thereof.

Such prior art technology makes it possible to increase kink resistance in a state in which the guidewire is contained in the catheter, that is, inside the guide catheter. The drawback of that technology was that when the guidewire was inserted, the catheter could be easily bent in the joining region of the medium portion and base portion and operation ability by the operator was very poor.

Japanese Patent No. 2933389 (Balloon Catheter Comprising Inner Cavity for Guidewire on the Distal End Side) discloses a medical balloon catheter in which a transition portion extending from the distal end side of the opening of the proximal end inner cavity of the guidewire lumen to the vicinity of the distal end of the first shaft portion (proximal end shaft in accordance with the present invention) has a rigidity between that of the first shaft portion and second shaft portion (distal end shaft in accordance with the present invention).

This prior art technology provides a catheter shaft with increased kink resistance, but this increase in kink resistance is implemented by additionally providing the second shaft with a coil-like member as a deformation preventing structure. The problem associated with such additional coil-like member was that the number of operations during catheter manufacture was greatly increased and, at the same time, the assembly method was made difficult which resulted in the increased production cost. Further, with this prior art technology, the deformation preventing structure was mounted on the outer or inner side of the outer sleeve, or on the outer side of a core tube. When the deformation preventing structure was mounted on the outer side of the outer sleeve, the increase in the outer diameter of the outer sleeve could degrade crossability, and when the deformation preventing structure was mounted on the inner side of the outer sleeve or on the outer side of the cure tube, the inflation lumen was locally narrowed, producing an adverse effect on dilation or contraction behavior of the balloon.

Further, Japanese Patent Publication No. 6-507105 (Vascular Catheter Comprising Guidewire Proximal End Cavity and Intermediate Member" discloses a vascular catheter comprising a main shaft (proximal end shaft in accordance with the present invention), a balloon, a plastic shaft portion (distal end shaft in accordance with the present invention) located between the main shaft and the balloon, an intermediate member mounted on the main shaft, extending inside the plastic shaft portion in the distal end direction and having a rigidity not higher than that of the main shaft portion, and a guidewire lumen, wherein the guidewire inlet is withdrawn from the distal end of the main shaft portion in the proximal end direction.

Such prior art technology provides a vascular catheter with improved pushability and trackability and also increased kink resistance. However, kink resistance demonstrated when the vascular catheter is inserted into the guide catheter along the guidewire can hardly be considered good. In order to further increase kink resistance, it is necessary to enlarge the diameter of the core wire used as a non-rigid intermediate member. However, in order to ensure the effective inflation lumen, the increase in the profile of the catheter shaft is required, and the decrease in crossability and trackability causes concerns.

Examined Japanese Patent Application No. 4-44553 (Catheter Equipped with Balloon) discloses a catheter equipped with a balloon comprising a rigidity increasing member which extends in the axial direction in the outer tube and provides it with rigidity and a portion comprising no such rigidity increasing member at the distal end of he outer tube.

On the other hand, a balloon catheter is used to conduct dilatotherapy mainly by inserting the catheter into the body passage which is the object of therapy and introducing the internal pressure into the therapy zone. Therefore, the required mechanical properties include a strength sufficient to prevent rupture of the balloon when a pressure necessary for the dilation is introduced and a capability to control the balloon safely to the desired dilation size. Furthermore, in most cases, in order to conduct therapy in a vascular system, the catheter has to be inserted to the zone of pathology changes and prescribed position along the blood vessel and the operation ability of the distal end portion of the catheter for such an insertion is very important.

The catheter is typically composed of thin tubular members and has to be passed through the curved zones inside the body or narrow stenotic zones by operating the catheter from outside of the body through the insertion opening into the body. Accordingly, a small size of the catheter itself, in particular, of the distal end thereof is very important. In addition, a force applied to the catheter from outside of the body has to be effectively transmitted to the distal end portion and flexibility is required to adapt to the cured portions. Further, because guidewire is usually used by being passed inside the catheter, a small friction resistance between the catheter and guidewire is also an important property allowing for smooth movement of the catheter without disrupting the force transmission. In order to obtain such an operation ability, the structure of a typical balloon catheter is required to have the following properties: (1) flexibility of the distal end (far end) portion allowing the catheter to follow the curved internal passages, (2) strength of the proximal end (near end) portion sufficient to provide for good transmission of force to the distal end, and (3) low friction and high sliding ability of the tube used for passing a guidewire in order to suppress friction resistance. Catheters satisfying those requirements are most often made of polyethylene, high-strength polyamide, or high-strength polyamide elastomers.

With respect to thinness and flexibility, a small size and flexibility of the balloon portion at the distal end of the catheter and in the vicinity thereof are the especially important properties. Furthermore, because this portion is often inserted into the curved portions or slides over the softest portion of the guidewire inserted therein, the absence of discontinuity in this flexibility is also required. Thus, when the catheter is disposed in a curved portion, if the flexibility is discontinuous, bending of the catheter becomes discontinuous, and guidewire resistance in this portion greatly increases causing degradation of operation ability.

Further, a fixed portion of the tube for passing the balloon and guidewire is typically present as the distalmost portion "tip" at the de of balloon catheter. When this tip portion is hard, the difference in flexibility with the guidewire let out of the tip increases and guidewire can be easily bent in this zone, becoming a serious cause of operation ability degradation. Furthermore, in case of zone of pathological changes with advanced calcification, the following effects are of frequent occurrence. Thus, when an attempt is made to pass a balloon catheter along the guidewire that has been passed through such a zone, if the distal end is not sufficiently thin, it is obstructed by the hard zone of pathological changes and is not able to pass therethrough, or if the tip portion is hard, it is caught by the hard zone of pathological changes and is not able to pass therethrough.

Furthermore, in recent years, metallic stationary dilators typically called stents are often used in vascular dilation therapy. In order to conduct shape dilation after stent dilation (post-dilation) and also in case of re-stenosis inside the stents and stenosis at the distal end side of the stents, the balloon catheter has to be passed inside the stents. However, in such a case, similarly to the zones of pathological changes with advanced calcification, the problem was that if the distal end was not sufficiently small and the tip portion was hard, the catheter was caught by the metallic stent and could not pass therethrough.

DISCLOSURE OF THE INVENTION

With the prior art technology described in the aforesaid open publications, kink resistance was increased by using an outer tube with good trackability that had a member increasing rigidity thereof. However, when the outer tube itself has a high kink resistance, or when a high kink resistance is provided with a reinforcing member such as a metal wire and the like disposed inside the outer tube, the rigidity of the outer tube is locally increased, but the kink resistance of the entire catheter shaft is difficult to increase. Further, the problem associated with providing an additional component, as shown in the embodiment of the prior art technology in which a wire braid was embedded in a plastic outer tube, is that the number of production process operations was increased and production cost was raised.

This first problem can be resolved by providing a medical balloon catheter which is easy to assemble and in which the rigidity of catheter shaft is caused to change continuously in the longitudinal direction of the catheter shaft and pushability and kink resistance are increased, while the profile of a catheter shaft is being held to a minimum and crossability and trackability are being maintained.

The present invention based on the results of a comprehensive study conducted to resolve the aforesaid first problem provides a medical balloon catheter comprising a catheter shaft composed of a distal end shaft and a proximal end shaft, a balloon on the distal end of the distal end shaft, and a hub provided with a port for supplying pressure fluid to the balloon on the proximal end of the proximal end shaft, wherein the distal end shaft comprises a guidewire lumen and an inflation lumen for dilating the balloon on the inner surface, the proximal end shaft is composed of a simple member and at the same time comprises the inflation lumen on the inner surface, the distal end portion of the proximal end shaft has a rigidity lower than other parts of the proximal end shaft, and the distal end shaft and the proximal end shaft are joined together outside the distal end portion of the proximal end shaft. It is preferred that part of the distal end portion of the proximal end shaft overlap the guidewire lumen and that the distal end shaft have a rigidity lower than that of the distal end portion of the proximal end shaft. Further, the rigidity of the distal end portion of said proximal end shaft may gradually decrease as the distal end side of the proximal end shaft is being approached.

A spiral notch is preferably provided on the distal end portion of the proximal end shaft. The pitch of the spiral in the spiral notch is preferably no more than 5 mm, more preferably, no more than 2 mm. The pitch of the spiral may gradually increase as the distal end side of the proximal end shaft is being approached.

The width of the spiral in the spiral notch is preferably no less than 0.5 mm and no more than 10 mm, more preferably, no less than 0.5 mm and no more than 5 mm. The width of said spiral may gradually decrease as the distal end side of the proximal end shaft is being approached.

Further, the pitch of said spiral may gradually increase as the distal end side of the proximal end shaft is being approached and the width of said spiral may gradually decrease as the distal end side of the proximal end shaft is being approached.

Slits may be present on the distal end portion of said proximal end shaft instead of the spiral notch, and the slits can be present along either the axial direction or circumferential direction of the proximal end shaft. Further, grooves may be present on the distal end portion of said proximal end shaft instead of the spiral notch, and the grooves can be present along either the axial direction or circumferential direction of the proximal end shaft. Further, in addition, holes may be present in the proximal end shaft instead of the above-described notch, slits, and grooves.

The length of the distal end portion of the proximal end shaft is preferably no less than 30 mm, more preferably, no less than 50 mm.

The proximal end shaft is preferably composed of a metal tube. In this case, the proximal end shaft is preferably composed of stainless steel, more preferably, of stainless steel SUS316.

Further, as described hereinabove, it is important that the distal end portion of the balloon catheter, in particular, the portion from the tip portion to the balloon portion, be thin and flexible and have no significant different in hardness with other portions of the catheter. This is the second problem.

A method for adhesively fixing the balloon and the tube for passing a guidewire inside thereof with an adhesive and a method for fixing by fusion are used as methods for processing the tip portion. When an adhesive fixing method is used, an adhesive layer is present. By contrast, with the method employing fusion, the adhesion layer is not present. In addition, the diameter can be easily decreased by thermal processing during or after fusion. Therefore, the fusion method is effective in reducing the diameter, increasing flexibility, and reducing the discontinuity of flexibility. However, in the conventional catheters, polyethylene, which is a polyolefin material, in particular, high-density polyethylene with an excellent low-friction characteristic was most often used for the tube for passing a guidewire inside thereof (guidewire tube). High-density polyethylene is a material with excellent low-friction characteristic, but has poor fusibility and adhesive bondability with other materials and cannot be fused to any materials other than polyolefin materials. As a result, only adhesive bonding could be used for joining it to other materials. On the other hand, when a balloon from a polyolefin material was used, fusion could be employed. However, because a bridge to the balloon was required, the portion serving as fusion tolerance restricted a possible reduction in thickness. As a result, the fusion process, too, could not provide for reduction of diameter and increase in flexibility of the tip portion. Furthermore, because the high-density polyethylene with excellent low-friction characteristic has poor flexibility, the usage of a low-density polyethylene, which is a comparatively flexible material, for the guidewire tube has been considered. However, such a usage was practically impossible because friction properties and sliding properties rapidly degraded as the flexibility increased. When a high-density polyethylene single-layer tube was used as the guidewire tube, the tip portion was difficult to provide with sufficiently reduced diameter and increased flexibility.

There are commercial balloon catheters in which a two-layer tube with an outer layer from a polyamide and an inner layer of polyethylene is used as the tube for passing the guidewire inside thereof and the balloon is made of the polyamide with properties identical to those of the polyamide of the outer tube. However, because the elastic modulus of polyamides is typically higher than that of polyethylene, the tip portion could not be provided with sufficient flexibility.

Further, there are commercial balloon catheters comprising a balloon made of a polyamide elastomer and a guidewire tube fabricated from a polyamide elastomer with a hardness higher and melting point also higher than those of the polyamide elastomer of the balloon. However, because a material harder than the balloon was disposed in the guidewire tube, the tip portion did not have sufficient flexibility.

The second problem which is to be resolved by the present invention is to provide an improved medical balloon catheter which has excellent operation ability because the distal end portion of the distal end of the catheter has a sufficiently small diameter and sufficiently high flexibility and also because the discontinuity of flexibility is reduced.

Means for resolving the second problem are provided by selected dimensions, assembly method, and arrangement of materials.

Thus, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in the tube are fused together in the vicinity of the distal end of the catheter, wherein the ratio of the outer diameter of the small-diameter portion on the distal end side in the tube to the outer diameter of the proximal end portion, (outer diameter of the small-diameter portion on the distal end side)/(outer diameter of the proximal end portion), is no less than 0.85. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in the tube are fused together in the vicinity of the distal end of the catheter, wherein the Shore hardness of the material constituting at least that part of the small-diameter portion on the distal end side in the tube which is fused to the balloon is less than the Shore hardness of the material constituting the balloon. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in the tube are fused together in the vicinity of the distal end of the catheter, wherein the flexural modulus of elasticity of the material constituting at least that part of the small-diameter portion on the distal end side in said tube which is fused to the balloon is less than the flexural modulus of elasticity of the material constituting the balloon. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in the tube are fused together in the vicinity of the distal end of the catheter, wherein the melting point of the material constituting at least that part of the small-diameter portion on the distal end side in said tube which is fused to the balloon is lower than the melting point of the material constituting the balloon. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in the tube are fused together in the vicinity of the distal end of the catheter, wherein the outer diameter of the small-diameter portion on the distal end side in the tube is no more than 0.52 mm. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention has a structure in which the balloon is composed of a polyester elastomer material and at least that part of the small-diameter portion on the distal end side in said tube which is fused to the balloon is composed of a polyester elastomer material. With such a structure, fusion which is used as the fixing method producing no adhesive layer is facilitated, the tip portion can be adjusted to a flexible structure with small discontinuity of flexibility, and the above-mentioned problem is resolved.

Further, the medical balloon catheter in accordance with the present invention has a structure in which the balloon is composed of a polyamide elastomer material and at least that part of the small-diameter portion on the distal end side in said tube which is fused to the balloon is composed of a polyamide elastomer material. With such a structure, fusion which is used as the fixing method producing no adhesive layer is facilitated, the tip portion can be adjusted to a flexible structure with small discontinuity of flexibility, and the above-mentioned problem is resolved.

Further, the medical balloon catheter in accordance with the present invention has a structure in which the polyester elastomer material or the polyamide elastomer material has soft segments and hard segments in a molecule and the ratio of soft segments in the material constituting the balloon is less than the ratio of soft segments in the material constituting the tube for passing a guidewire inside thereof. With such a structure, the flexibility of the guidewire tube itself is increased, the tip portion can be adjusted to a flexible state, and the above-mentioned problem is resolved.

Further, with the medical balloon catheter in accordance with the present invention, in addition to the above-described effects inherent to the aforesaid balloon catheter, guidewire slidability can be increased by using a structure in which the innermost surface of the tube for passing a guidewire inside thereof is composed of high-density polyethylene.

Further, the medical balloon catheter in accordance with the present invention has a structure in which the tube for passing a guidewire inside thereof has a multilayer structure consisting of no less than two layers, the position which is to be fused is composed of a polyamide elastomer or a polyester elastomer, the innermost surface is composed of high-density polyethylene, and no less than one binder layer is present, if necessary, between the portion that has been fused and the innermost surface. With such a structure, both the excellent guidewire slidability and the fusibility with the guidewire tube can be provided and the above-mentioned problem is resolved.

Further, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in said tube are fused together in the vicinity of the distal end of the catheter, wherein that part of the small-diameter portion on the distal end side in the tube which is fused to the balloon is composed of a polyester elastomer having hard segments and soft segments in a molecule and the ratio of the soft segments is higher than 13%. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention is composed of a plurality of tubes and a balloon, this catheter having a structure in which a tube formed to have an outer diameter on the distal end side smaller than that on the proximal end side and serving as a tube for passing a guidewire inside thereof is arranged so as to pass inside the balloon and the balloon and the small-diameter portion on the distal end side in said tube are fused together in the vicinity of the distal end of the catheter, wherein that part of the small-diameter portion on the distal end side in the tube which is fused to the balloon is composed of a polyamide elastomer having hard segments and soft segments in a molecule and the ratio of the soft segments is higher than 14%. With such a structure, the tip portion can be adjusted to a flexible state by increasing the flexibility of the guidewire tube itself and by using fusion, which produces no adhesive layer, as a fixing method, and the above-mentioned problem is resolved.

Further, the medical balloon catheter in accordance with the present invention has a structure in which the proximal end of an X ray impermeable ring is abutted against and fixed to the boundary portion of the proximal end side and the small-diameter portion on the distal end side of the tube for passing a guidewire inside thereof. With such a structure, discontinuity of flexibility in the vicinity of the balloon can be reduced and the above-mentioned problem is resolved.

Further, the medical balloon catheter in accordance with the present invention has a structure in which the tube constituting the outer surface of the catheter is composed of a material that can be fused with the balloon and is fused and arranged on the proximal end side of the balloon. With such a structure, because no adhesive layer is formed, the distal end side of the balloon is flexible and discontinuity of flexibility can hardly occur therein. Therefore, the above-mentioned problem is resolved. An additional advantage from the production standpoint is gained when the above-described structures are employed in balloon catheters of a rapid exchange type, in which the guidewire tube is limited to a range from the distalmost end of catheter to the intermediate part of the outer tube, because the guidewire inlet portion can be formed by fusing the outer tube with the guidewire tube, process stability is superior to that of the molding process using adhesive bonding or the like, and the diameter of this portion can be reduced.

BEST MODE FOR CARRYING OUT THE INVENTION

Various embodiments of the medical balloon catheter in accordance with the present invention will be described below. First, the embodiments relating to a catheter shaft will be explained with reference to FIGS. 2 through 22.

Figure 1:
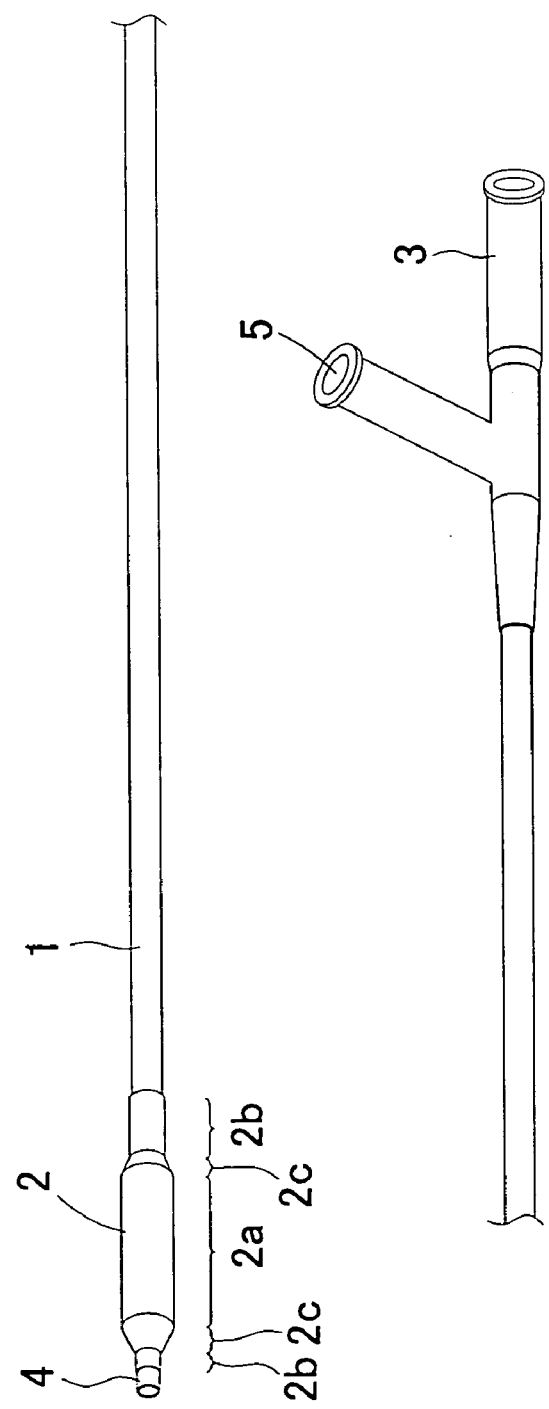
FIG. 1 is a schematic perspective view of a catheter of an over-the-wire type, among the typical balloon catheters for PTCA.
Figure 2:
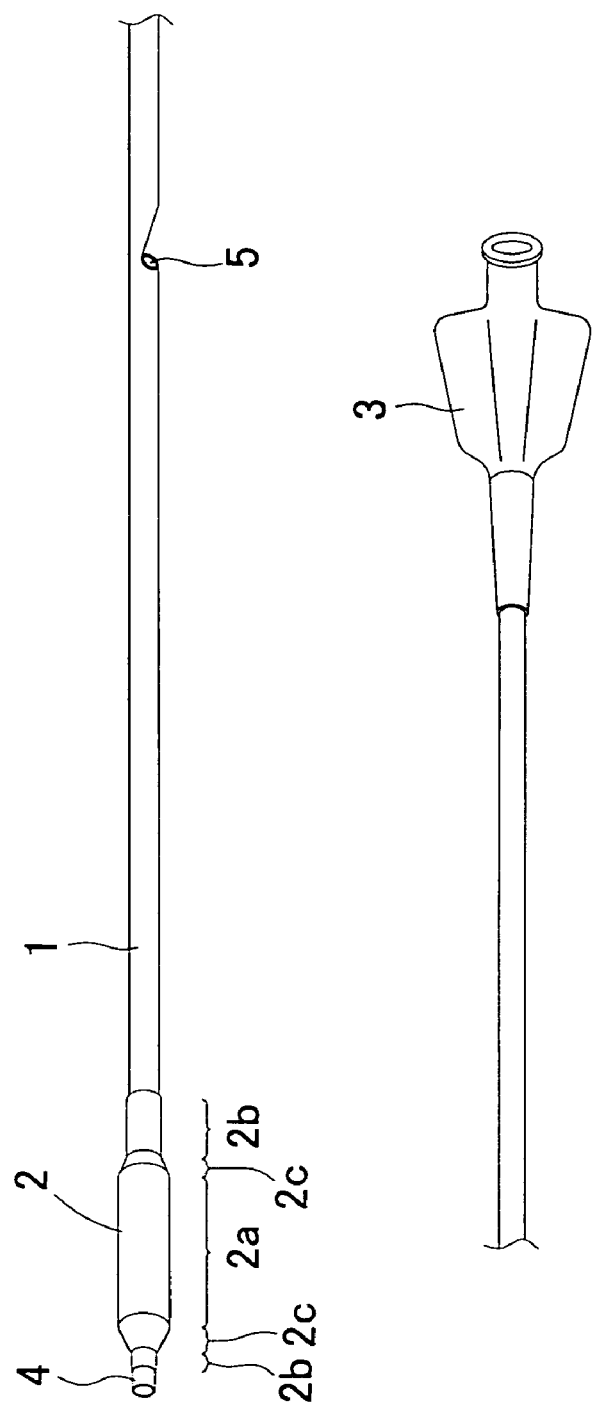
FIG. 2 is a schematic perspective view of a catheter of a rapid exchange type, among the typical balloon catheters for PTCA.
Figure 3:
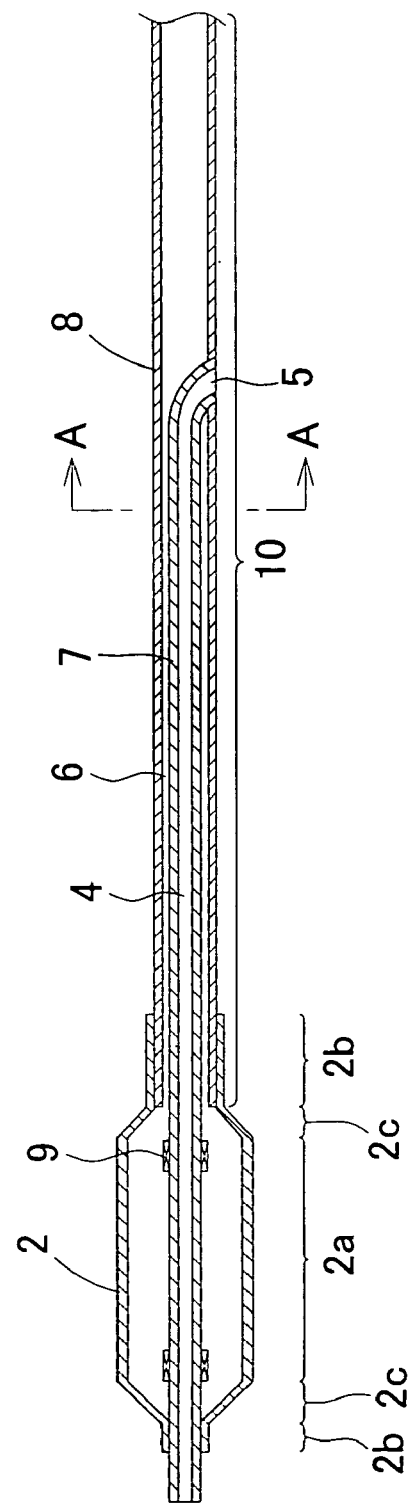
FIG. 3 is a schematic side view illustrating a cross section of a distal end shaft with a coaxial structure in the rapid exchange catheters which are the typical balloon catheters for PTCA.
Figure 4:
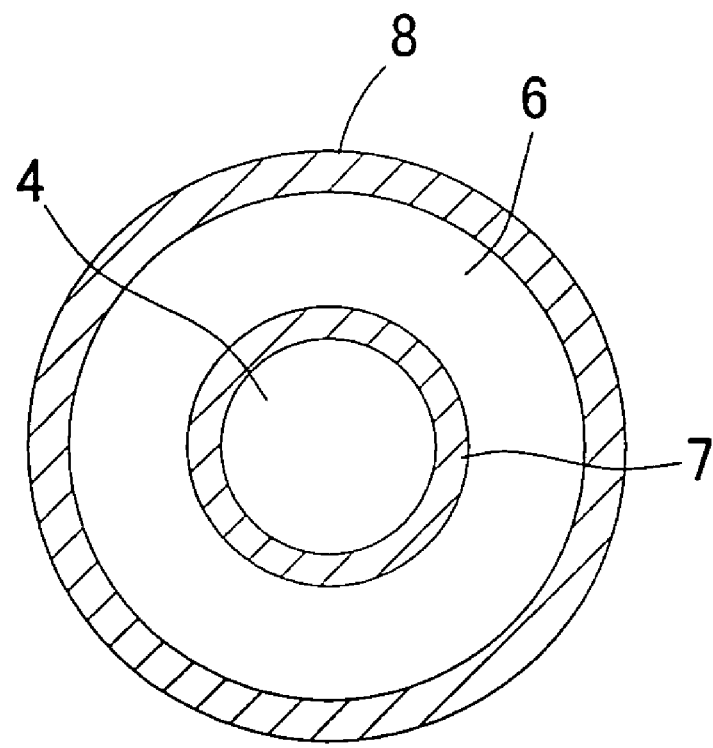
FIG. 4 is a cross-sectional view along the A-A' line in FIG. 3.
Figure 5:
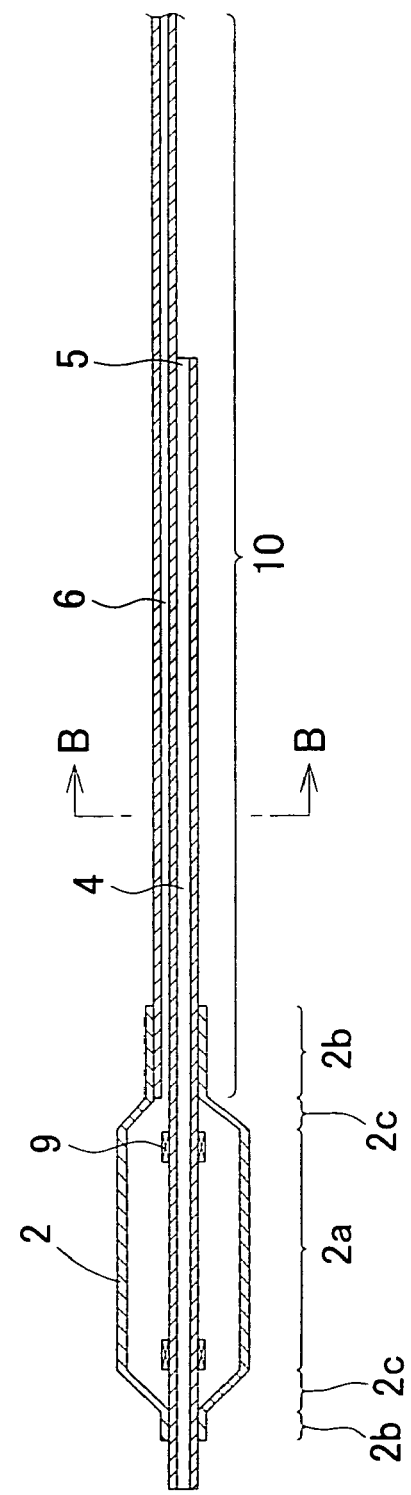
FIG. 5 is a schematic side view illustrating a cross section of a distal end shaft with a biaxial structure in the rapid exchange catheters which are the typical balloon catheters for PTCA.
Figure 6:
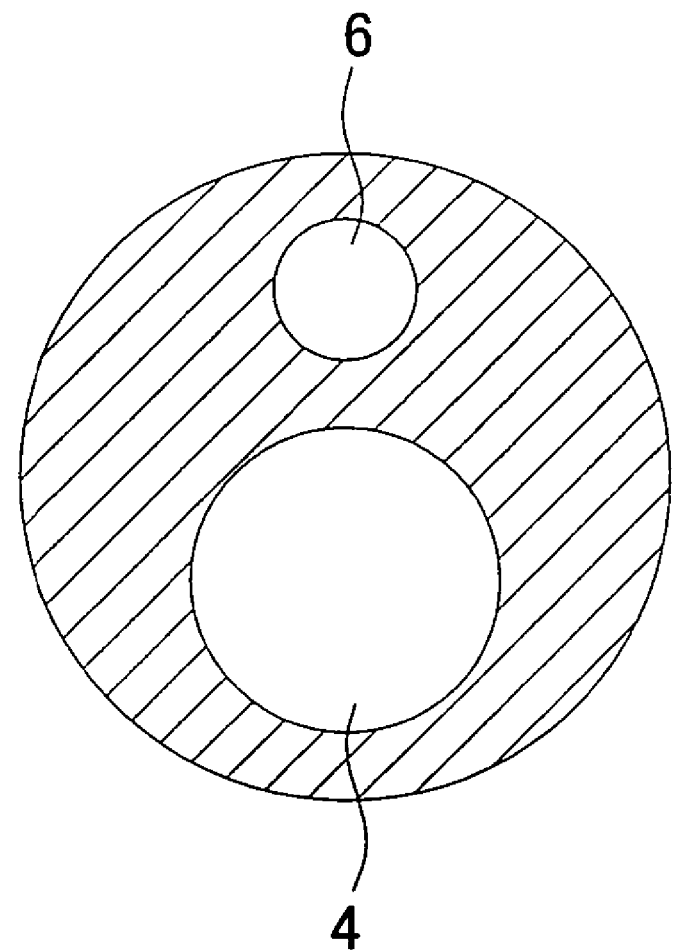
FIG. 6 is a cross-sectional view along the B-B' line in FIG. 5.

The medical balloon catheter of the present embodiment has a structure in which, as shown in FIG. 2, a balloon 2 is joined to a distal end of a catheter shaft 1 and a hub 3 for supplying pressure fluid for adjusting the internal pressure of the balloon is joined to the catheter shaft 1, and relates to a rapid exchange catheter in which a guidewire lumen 4 is provided only at the distal end side of the balloon catheter and a guidewire port 5 is provided in the medium portion of catheter shaft 1. The catheter shaft 1 of the present embodiment is composed of a distal end shaft 10 and a proximal end shaft 11 which are connected to each other in a joint zone 12. In this case, no limitation is placed on the structure of the distal end shaft 10, on condition that the guidewire lumen 4 and an inflation lumen 6 are provided therein. In other words, a coaxial structure may be employed in which, as shown in FIG. 3 and FIG. 4, an inner tube 7 and an outer tube 8 are installed so that the distal end shaft 10 has a coaxial double-wall configuration and which has the guidewire lumen 4 demarcated by the inner surface of the inner tube 7 and the inflation lumen 6 demarcated by the inner surface of the outer tube 8 and the outer surface of the inner tube 7, or a biaxial structure may be employed in which, as shown in FIG. 5 and FIG. 6, the guidewire lumen 4 and inflation lumen 6 are arranged in parallel. Other structures also place no limitation on the effect of the present invention. The reference symbol 9 in the figures stands for a ring impermeable to X rays.

The proximal end shaft 11 is composed of a single member, and a specific feature thereof is that the distal end portion 13 of the proximal end shaft 11 has a rigidity lower than that of the other parts of the proximal end shaft 11. No limitation is placed on means for reducing the rigidity of the distal end portion 13 of the proximal end shaft 11, and the rigidity of the distal end portion can be reduced by forming a spiral notch 14, slits 17, grooves 21, and holes 26. The optimum rigidity reduction means can be selected and implemented based on the target profile or application of the medical balloon catheter, processing cost, and the like.

No limitation is placed on the method for forming the spiral notch 14, slits 17, grooves 21, and holes 26, but from the standpoint of processing accuracy, the formation method using a laser is preferred. The type of the laser to be used can be determined and selected by taking into account the material of the proximal end shaft 11 and the like.

Figure 7:
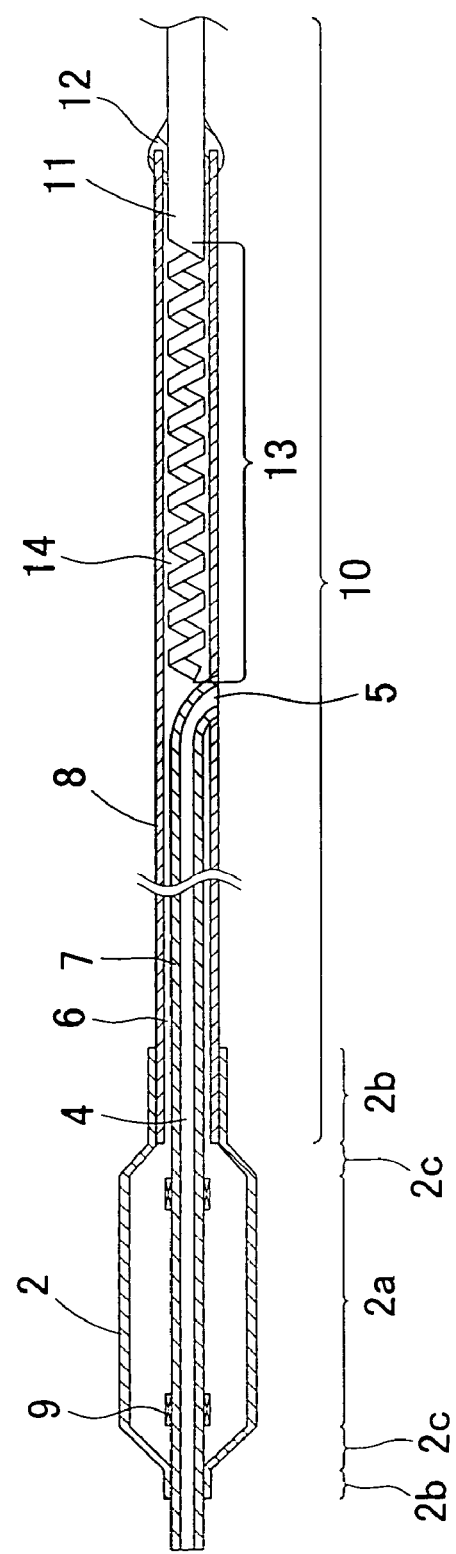
FIG. 7 is a schematic side view illustrating a case where a spiral notch is present on the distal end of a proximal end shaft in the medical balloon catheter in accordance with the present invention.
Figure 8:
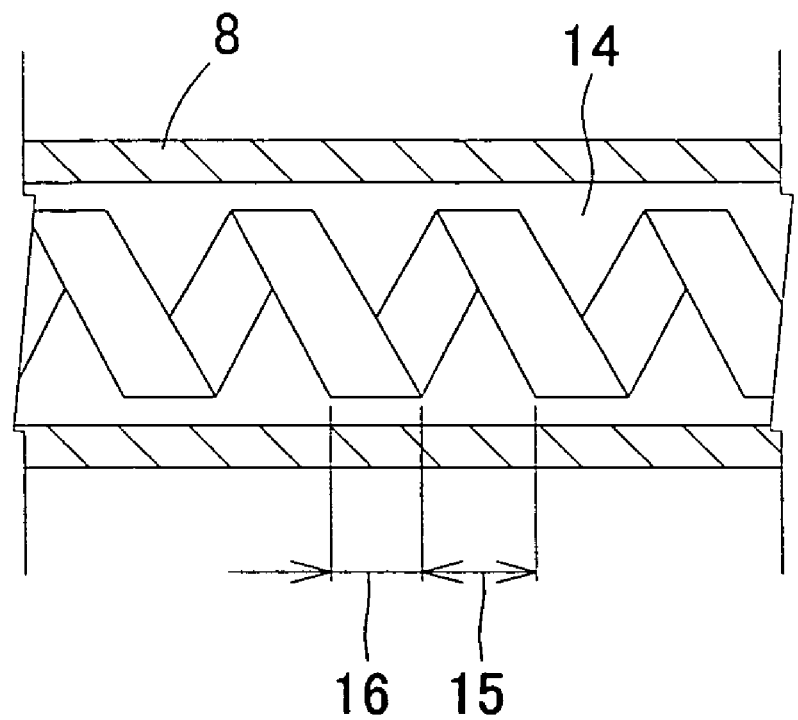
FIG. 8 is an expanded schematic side view of the spiral notch shown in FIG. 7.
Figure 9:
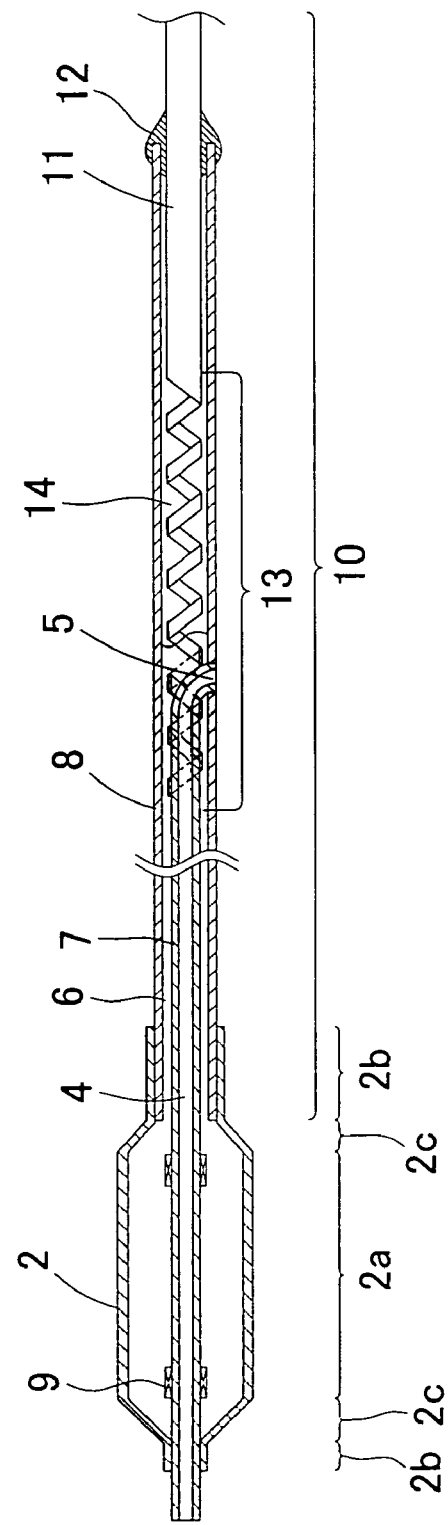
FIG. 9 is a schematic side view illustrating a case where a part of the distal end of a proximal end shaft and an inner cavity for passing a guidewire overlap in the medical balloon catheter in accordance with the present invention.

When the rigidity of the distal end portion 13 of the proximal end shaft 11 is reduced with a spiral notch 14, as shown in FIG. 7 and FIG. 8, a pitch 15 of the spiral is preferably no more than 5 mm. The pitch 15 of the spiral, as referred to herein, means the width of the notch in the axial direction of the shaft (see FIG. 8). When the pitch 15 of the spiral is greater than 5 mm, the rigidity of the proximal end shaft 11 decreases abruptly in the distal end portion 13, and the increase in pushability and kink resistance, which is the object of the present invention, is difficult to attain.

Because the rigidity of the proximal end shaft 11 is determined by the profile and material, the rigidity of the distal end portion 13 of the proximal end shaft can be optimized by changing the pitch 15 of the spiral according to the application of the medical balloon catheter. With consideration for the profile required for the proximal end shaft 11 when the medical balloon catheter is designed for PTCA, it is preferred that the pitch 15 of the spiral be no more than 2 mm. When the rigidity is thus optimized, a portion of the distal end of proximal end shaft 11 may overlap the guidewire lumen 4.

The pitch 15 of the spiral can be gradually increased as the distal end side of the proximal end shaft 11 is being approached in order to realize a medical balloon catheter in which continuous distribution of rigidity in the entire catheter shaft is obtained due to gradual reduction of rigidity of distal end portion 13 of the proximal end shaft 11 toward the distal end of the proximal end shaft 11 and which has even better kink resistance. In this case, the degree of gradual increase in the pitch 15 of the spiral can be adjusted and optimized by taking into account the rigidity of proximal end shaft 11 and distal end shaft 10.

Further, when the rigidity of the distal end portion 13 of the proximal end shaft is reduced by the above-mentioned spiral notch, it is preferred that the width 16 of the spiral be of no less than 0.5 mm and of no more than 10 mm. The width 16 of the spiral as referred to herein means the width of the portion sandwiched between the notches in the axial direction of the shaft. When the width 16 of the spiral is less than 0.5 mm, the rigidity decreases abruptly in the distal end portion 13 of the proximal end shaft and the kink resistant is difficult to increase. Furthermore, when the width 16 of the spiral exceeds 10 mm, the rigidity changes at the distal end side more abruptly than in the proximal end shaft 11 and the continuous distribution of rigidity is difficult to realize.

Because the rigidity of the proximal end shaft 11 is determined by the profile and material, the rigidity of the distal end portion 13 of the proximal end shaft can be optimized by changing the width 16 of the spiral according to the application of the medical balloon catheter. With consideration for the profile required for the proximal end shaft 11 when the medical balloon catheter is designed for PTCA, it is preferred that the width 16 of the spiral be no less than 0.5 mm and no more than 5 mm. When the rigidity is thus optimized, a portion of the distal end of proximal end shaft 11 may overlap the guidewire lumen 4.

The width 16 of the spiral can be gradually decreased as the distal end side of the proximal end shaft 11 is being approached in order to realize a medical balloon catheter in which continuous distribution of rigidity in the entire catheter shaft is obtained due to gradual reduction of the rigidity of distal end portion 13 of the proximal end shaft toward the distal end of the proximal end shaft 11 and which has even better kink resistance. In this case, the degree of gradual decrease in the width 16 of the spiral can be adjusted and optimized by taking into account the rigidity of proximal end shaft 11 and distal end shaft 10. Moreover, the rigidity of distal end portion 13 of the proximal end shaft may be also optimized by gradually increasing the pitch 15 of the spiral as the distal end of the proximal end shaft 11 is being approached and by gradually decreasing the width 16 of the spiral as the distal end of the proximal end shaft 11 is being approached.

Figure 10:
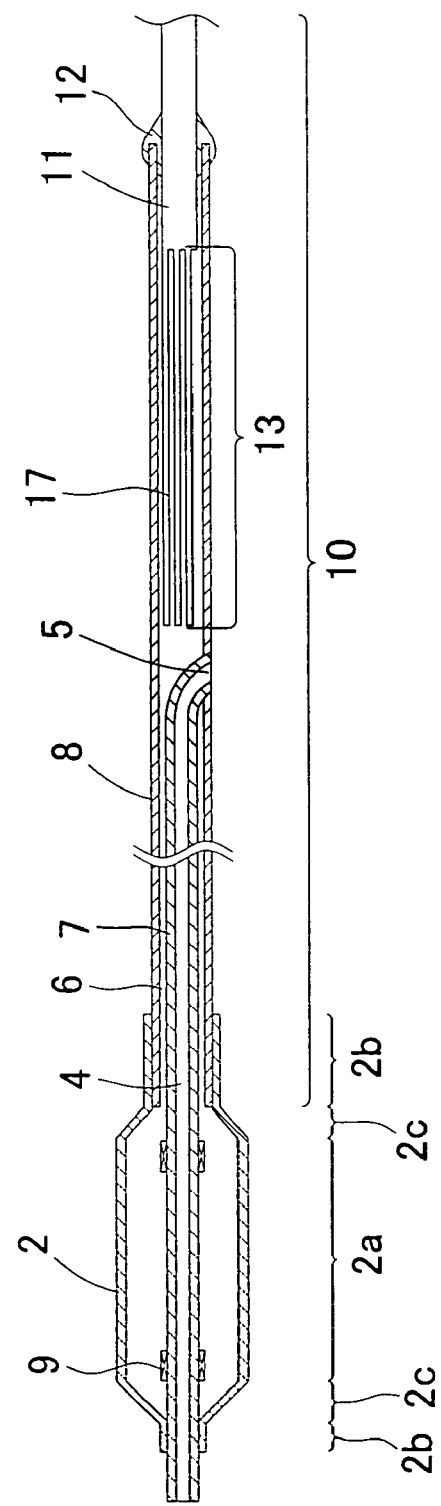
FIG. 10 is a schematic side view illustrating a case where slits are present in the axial direction on the distal end of a proximal end shaft in the medical balloon catheter in accordance with the present invention.
Figure 11:
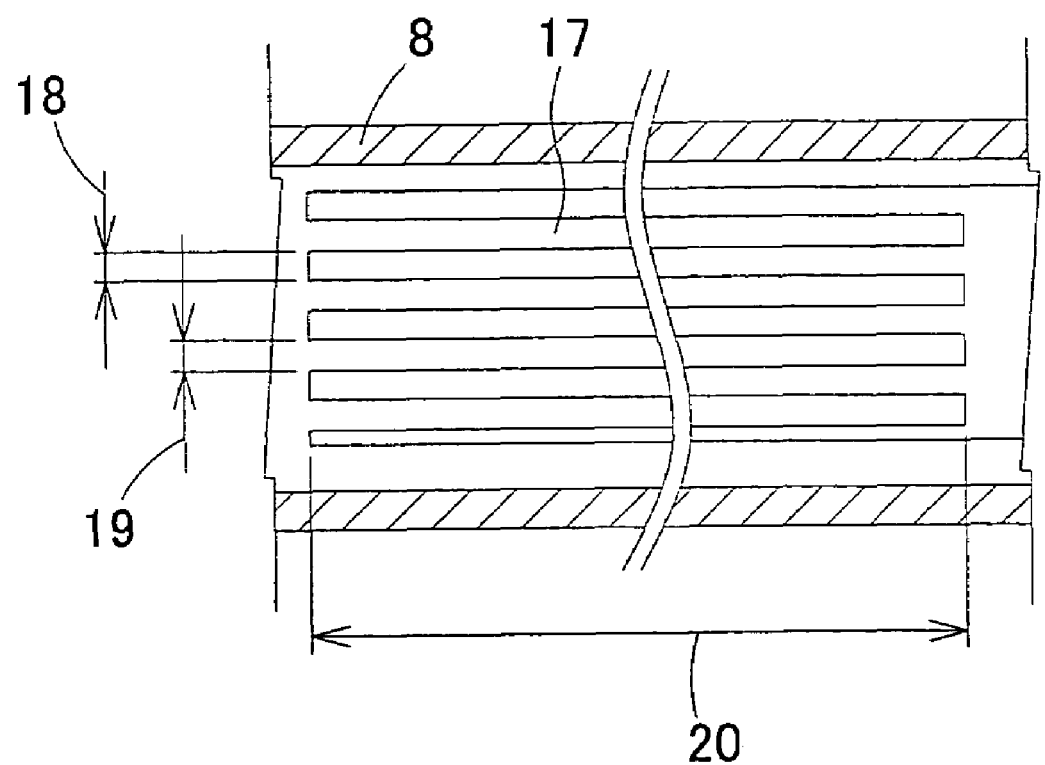
FIG. 11 is an expanded schematic side view of the slits shown in FIG. 10.
Figure 12:
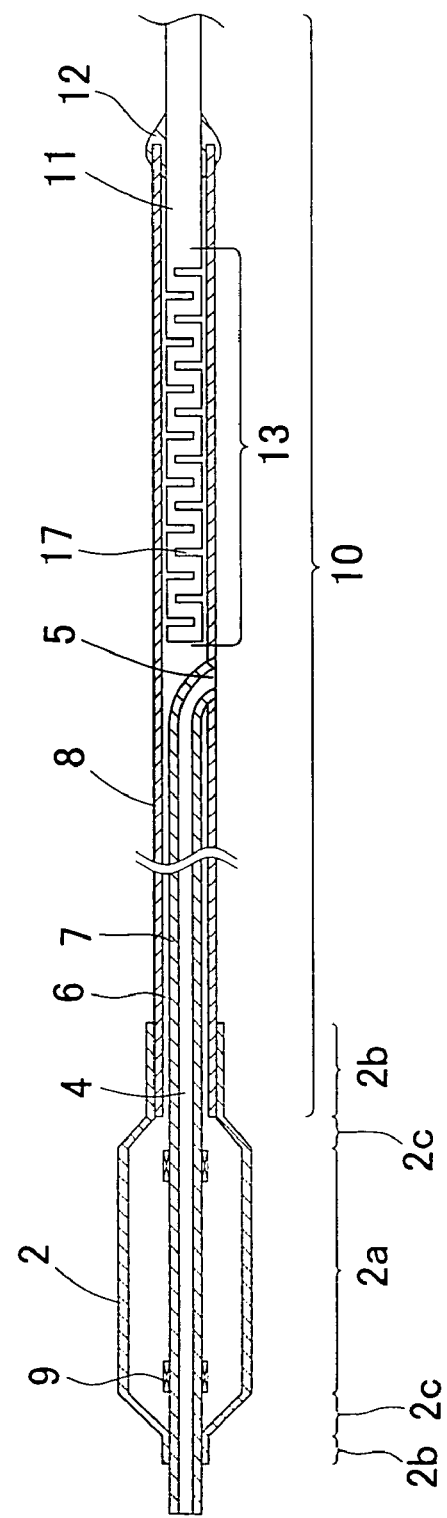
FIG. 12 is a schematic side view illustrating a case where slits are present in the circumferential direction on the distal end of a proximal end shaft in the medical balloon catheter in accordance with the present invention.
Figure 13:
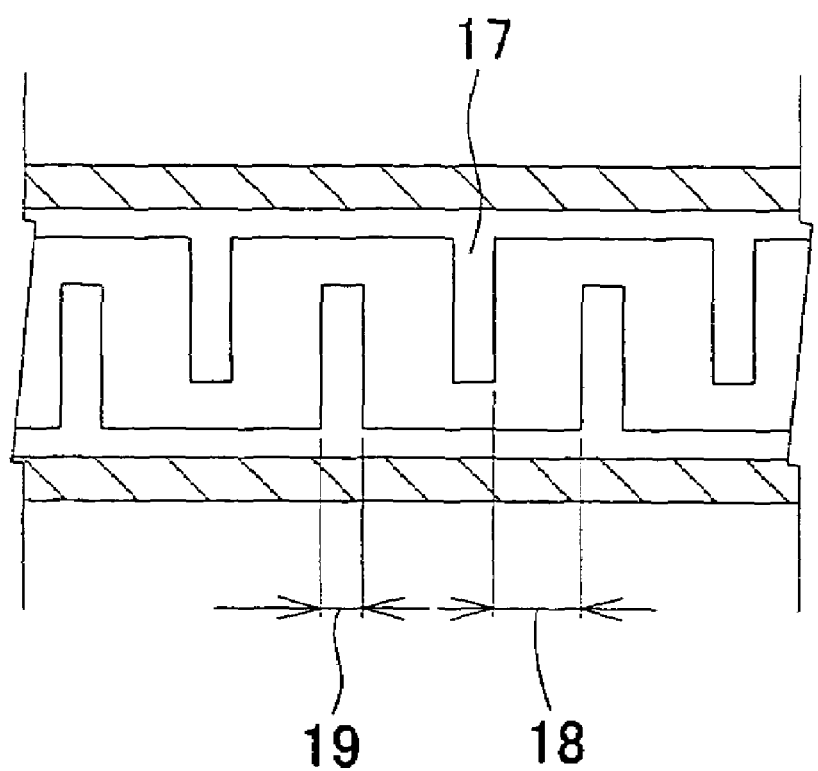
FIG. 13 is an expanded schematic side view of the slits shown in FIG. 12.
Figure 14:
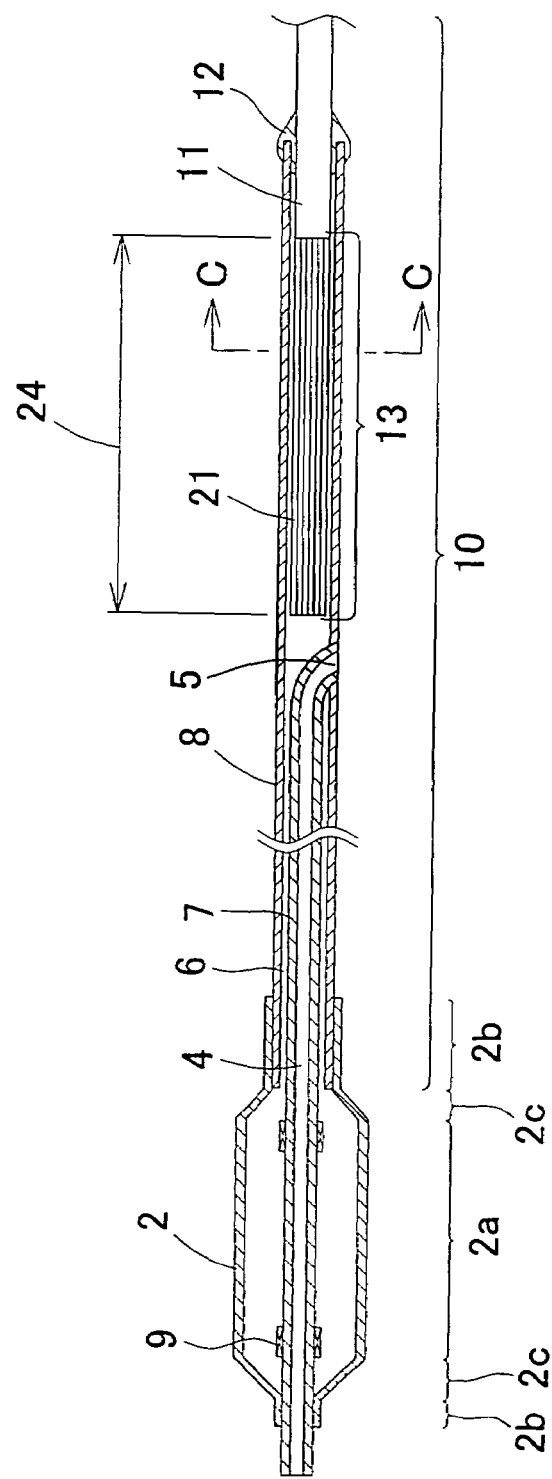
FIG. 14 is a schematic side view illustrating a case where grooves are present in the axial direction on the distal end of a proximal end shaft in the medical balloon catheter in accordance with the present invention.
Figure 15:
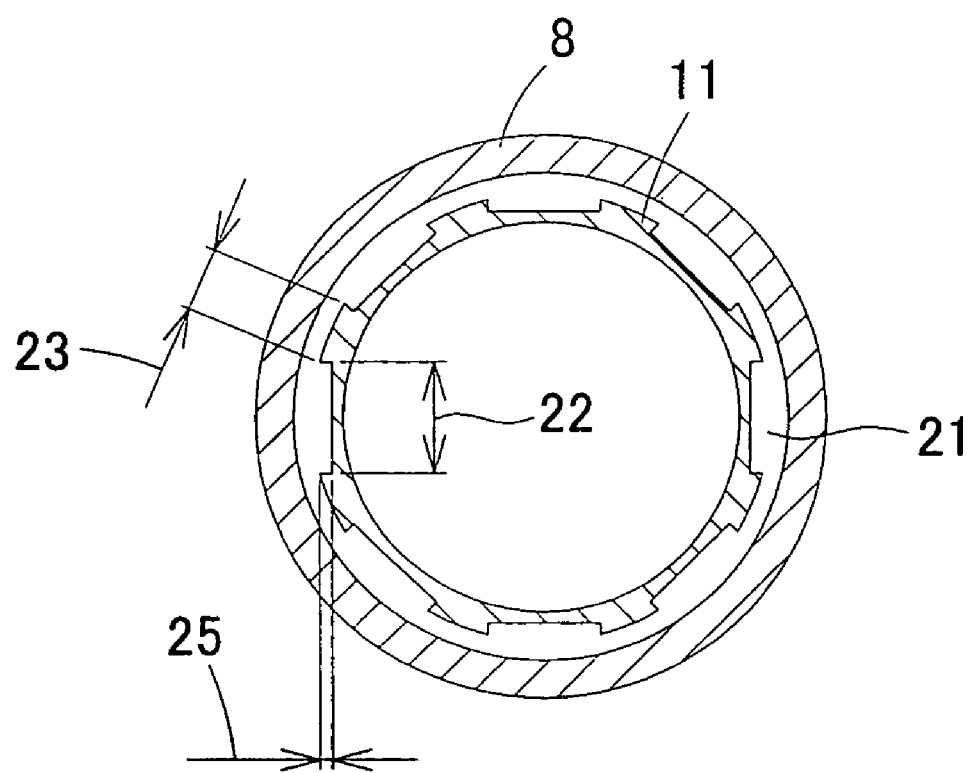
FIG. 15 is a cross-sectional view along the C-C' line in FIG. 14.
Figure 16:
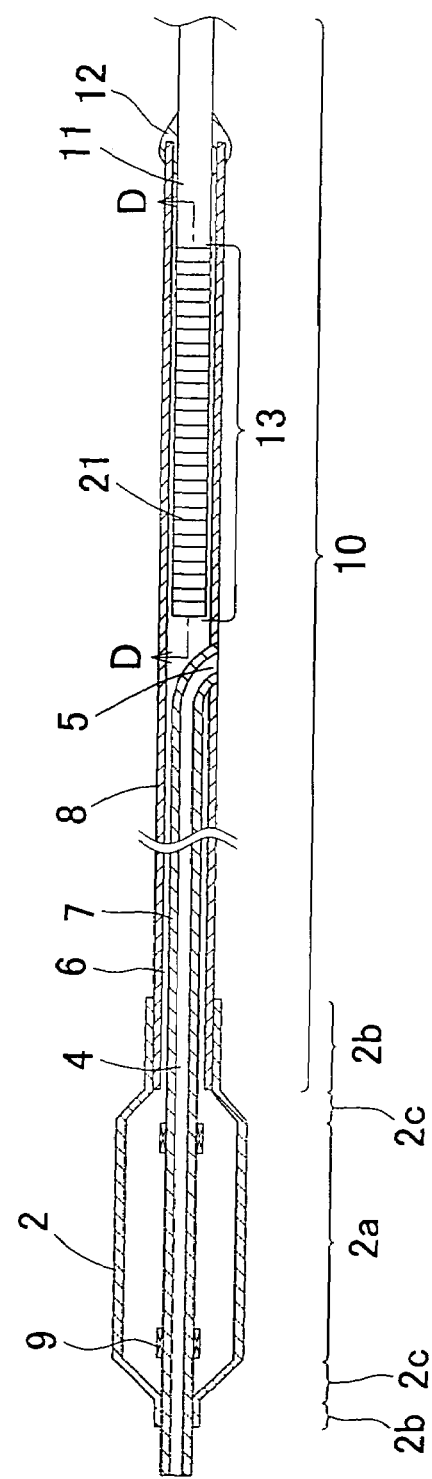
FIG. 16 is a schematic side view illustrating a case where grooves are present in the circumferential direction on the distal end of a proximal end shaft in the medical balloon catheter in accordance with the present invention.
Figure 17:
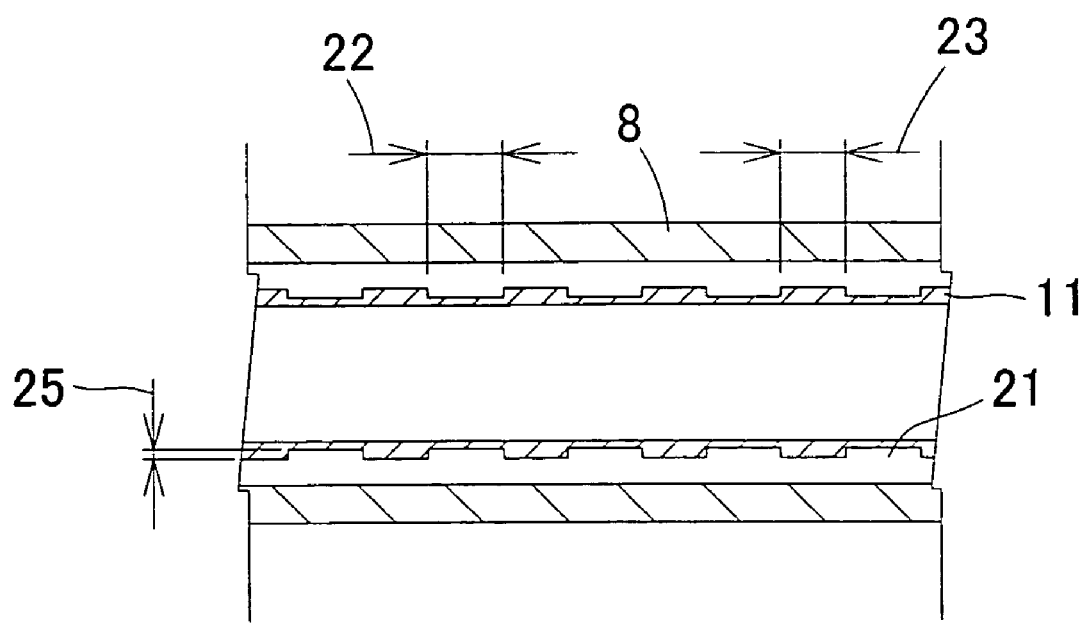
FIG. 17 is a cross-sectional view along the D-D' line in FIG. 16.

When the rigidity of the distal end portion 13 of the proximal end shaft is reduced with slits 17, as shown in FIGS. 10 through 13, the slits may be present in either the axial direction or circumferential direction of the proximal end shaft. As shown in FIG. 10 and FIG. 11, when the slits are present in the axial direction, a more continuous distribution of rigidity in the entire catheter shaft can be obtained by changing the spacing 18, width 19, and length 20 of the slits. When the slits are present in the circumferential direction, as shown in FIG. 12 and FIG. 13, the same effect can be produced by changing the spacing 18 and width 19 of the slits.

Figure 18:
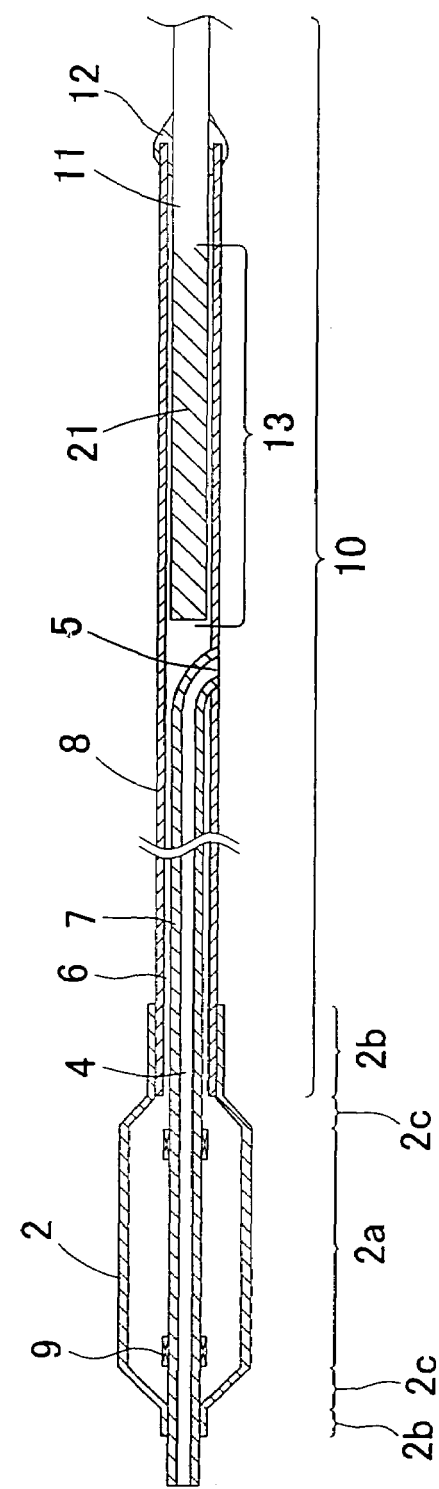
FIG. 18 is a schematic side view illustrating a case where spiral grooves are present on the distal end of a proximal end shaft in the medical balloon catheter in accordance with the present invention.

Further, when the rigidity of the distal end portion 13 of the proximal end shaft is reduced with grooves 21, as shown in FIGS. 14 through 18, the grooves 21 may be present in either the axial direction (see FIGS. 14 and 15) or circumferential direction (see FIGS. 16 and 17) of the proximal end shaft or may be in the form of a spiral (see FIG. 18). A more continuous distribution of rigidity in the entire catheter shaft can be obtained by changing the width 22, spacing 23, and length 24 of the grooves, in the same manner as discussed with reference to slits 17.

Figure 19:
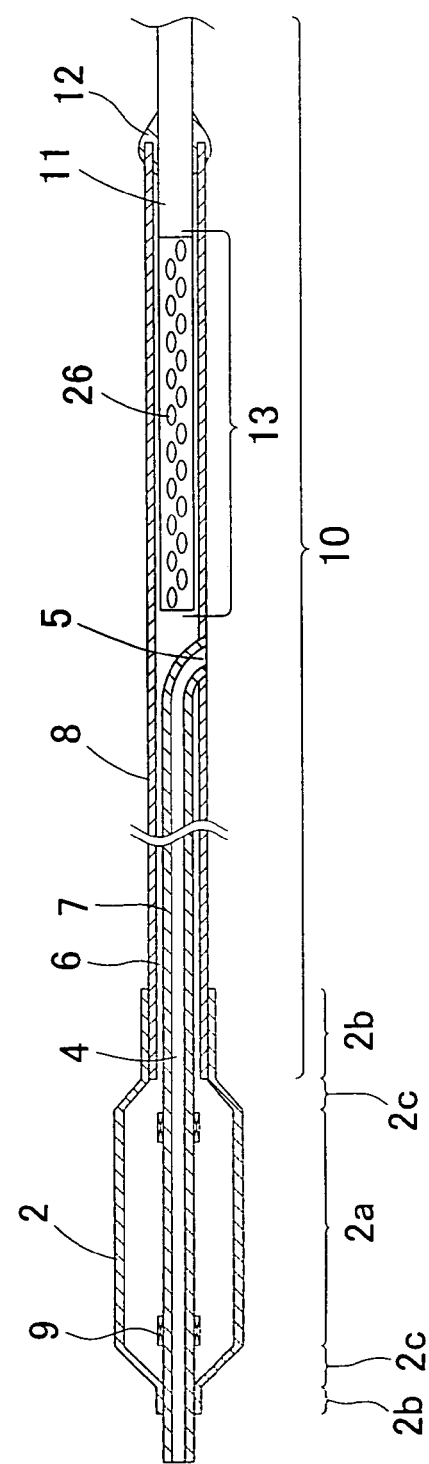
FIG. 19 is a schematic side view illustrating a case where holes are present on the distal end of a proximal end shaft in the medical balloon catheter in accordance with the present invention.

When the rigidity of the distal end portion 13 of the proximal end shaft is reduced with holes 26, as shown in FIG. 19, a more continuous distribution of rigidity in the entire catheter shaft can be obtained by changing the shape, size, and spacing of holes 26, in the same manner as discussed with reference to slits 17 or grooves 21.

The length of the distal end portion 13 of the proximal end shaft 11 is preferably no less than 30 mm. When it is less than 30 mm, changes of the rigidity of the distal end portion 13 of the proximal end shaft 11 become abrupt and sufficient kink resistance is difficult to realize. As described above, because the rigidity of the distal end shaft 11 is determined by the profile and material, the rigidity of the distal end portion 13 of the proximal end shaft 11 can be optimized by changing the length of the distal end portion 13 of the proximal end shaft 11. With consideration for the profile required for the proximal end shaft 11 when the medical balloon catheter is designed for PTCA, it is especially preferred that the length of the distal end portion 13 of the proximal end shaft 11 be no less than 0.5 mm and no more than 50 mm.

A specific feature of the present invention is that the distal end shaft 10 and proximal end shaft 11 are joined outside the distal end portion 13 of the proximal end shaft. The reference symbol 12 in the figures denotes the joint zone of the distal end shaft 10 and proximal end shaft 11. Spiral notch 14, slits 17, grooves 21, holes 26, or the like are provided to change continuously the rigidity of the distal end portion 13 of the proximal end shaft 11. In particular, if the distal end shaft 10 is joined in the distal end portion 13 of the proximal end shaft 11, when through passages are made in the wall surface of the proximal end shaft 11, as in the case of spiral notch 14, slits 17, and holes 26, a liquid-tight structure of the inflation lumen 6 of the medical balloon catheter is difficult to obtain and the balloon cannot be caused to expand or contract.

No limitation is placed on the method for joining the distal end shaft 10 and proximal end shaft 11. In other words, well-known technology can be used therefor. For example, adhesive bonding with an adhesive or fusion, if the distal end shaft 10 and proximal end shaft 11 are fusible, can be used. Furthermore, no limitation is placed on the composition, chemical structure or curing system of the adhesive used for joining. In other words, in terms of composition and chemical structure, adhesives of urethane, silicone, epoxy, cyanoacrylate, and other types can be used. In terms of curing system, adhesives of two-liquid mixed type, UV-curable adhesives, adhesives curable by water absorption, heat-curable adhesives, radiation-curable adhesives, and the like can be used. It is preferred that the adhesive have a hardness after curing such that the rigidity of the joint zone 12 of the distal end shaft 10 and proximal end shaft 11 do not change discontinuously via the adhesive bonding zone, and the adhesive can be selected by taking into account the rigidity of the distal end shaft 10 and proximal end shaft 11.

Figure 20:
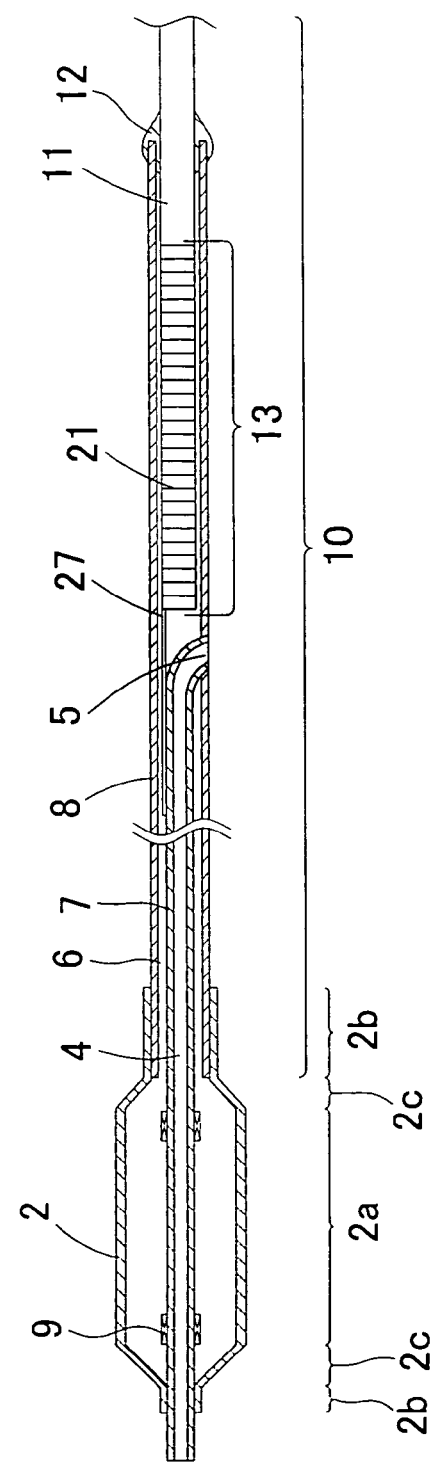
FIG. 20 is a schematic side view illustrating a case where grooves are present in the circumferential direction on the distal end of a proximal end shaft and a core wire is provided in the medical balloon catheter in accordance with the present invention.

In accordance with the present invention, the rigidity of the distal end shaft 10 is preferably lower than that of the distal end portion 13 of the proximal end shaft. As a result, the distribution of rigidity in the lengthwise direction of the medical balloon catheter is such that the rigidity gradually decreases toward the distal end of the medical balloon catheter and a contribution is made to the increase of kink resistance and, at the same time, to the improvement of trackability. However, when the rigidity of the distal end shaft 10 is too low by comparison with that of the distal end portion 13 of proximal end shaft 11, though the distribution of rigidity in the lengthwise direction of the medical balloon catheter is a gradually decreasing one, the degree of gradual decrease increases. As a result the kink resistance can be reduced. In such a case, as shown in FIG. 20, the rigidity can be adjusted by arranging a core wire 27 inside the distal end shaft 10. The core wire 27 as referred to herein means a member mounted on the proximal end shaft 11, distal end shaft 10, or hub 3 and extending inside the distal end shaft 10 toward the distal end.

When the rigidity of the distal end shaft 10 is higher than that of the distal end portion 13 of the proximal end shaft 11, the lowest rigidity of the catheter shaft is in the distal end portion 13 of the proximal end shaft 11 and the distribution of rigidity becomes discontinuous. Such a discontinuity not only reduces the kink resistance, but also causes the decrease in pushability and trackability and degrades the performance of the medical balloon catheter as a whole.

From the standpoint of crossability, it is advantageous that the profile of the distal end shaft 10 be as small as possible, but the profile has to be determined by taking into account the rigidity, cross sectional area of inflation lumen 6, cross sectional area of guidewire lumen 4, diameter of the guidewire used in the catheter, and the like. The profile changes depending on the usage and application of the medical balloon catheter, but the outer diameter is 0.75-3.00 mm, preferably, 0.80-2.50 mm.

Similarly, from the standpoint of crossability, it is advantageous that the profile of the proximal end shaft 11 be as small as possible, but the profile has to be determined by taking into account the rigidity distribution, cross sectional area of inflation lumen 6, and the like. The profile changes depending on the usage and application of the medical balloon catheter, but the outer diameter is 0.55-2.00 mm, preferably, 0.60-1.50 mm.

Dipping molding, blow molding, and the like are used as method for the manufacture of balloon 2 that can be inflated or contracted by internal pressure adjustment and is provided on the distal end of the distal end shaft 10, and the appropriate method can be selected according to the usage and application of the medical balloon catheter. In case of medical balloon catheters designed for dilatotherapy of stenotic portions of blood vessels or body cavities, blow molding is preferred because it provides for sufficient resistance to pressure. As an example, first, a tubular parison of any size is molded by extrusion molding or the like. This tubular parison is placed in a die having a mold matching in shape the balloon and stretched in the axial direction and radial direction by a biaxial stretching process. To mold a balloon of the same shape as that of the die. The biaxial stretching process may be conducted under heating or repeated several times. Furthermore, axial stretching and radial stretching may be conducted simultaneously or sequentially. Further, the balloon may be subjected to annealing to stabilize the shape and size of the balloon.

The balloon 2, as shown in FIG. 2 and FIG. 3, comprises a straight tubular portion 2a and joining portions 2b, 2b for conducting liquid-tight joining at the distal end side and proximal end side of the straight tubular portion. Tapered portions 2c are provided between the straight tubular portion 2a and joining portions 2b. The size of balloon 2 is determined by the usage and application of the medical balloon catheter. The outer diameter of straight tubular portion 2a in the balloon inflated by the internal pressure adjustment is 1.50-35.00 mm, preferably 1.50-30.00, and the length of straight tubular portion 2a is 10.00-80.00 mm, preferably, 10.00-60.00 mm.

No limitation is placed on the resin material of the tubular parison. Examples of suitable materials include polyolefins, polyolefin elastomers, polyesters, polyester elastomers, polyamides, polyamide elastomers, polyurethanes, polyurethane elastomers, and the like. Blended materials prepared by blending two or more of those resin materials or multilayer structures obtained by lamination of two or more thereof may be also used.

No limitation is placed on the material of the proximal end shaft 11. Examples of suitable materials include polyolefins, polyolefin elastomers, polyesters, polyester elastomers, polyamides, polyamide elastomers, polyurethanes, polyurethane elastomers, polyimides, polyimidoamides, polyetherimides, polyetherketones, polyetheretherketones, metals of a variety of types, and the like. However, when a balance of continuity of rigidity distribution in the entire medical balloon catheter, pushability, trackability, and the like is taken into account, it is preferred that a metal tube be used. From the standpoint of production cost, it is more preferred that the metal be a stainless steel tube, and with consideration for rigidity of the proximal end shaft 11 itself, it is even more preferred that stainless steel SUS316 be used. Further, when the above-mentioned resin materials are used for the proximal end shaft 11, the rigidity may be adjusted by arranging a core wire 27 inside the proximal end shaft 11 or in the proximal end shaft 11 and distal end shaft 10 to provide for the continuity of rigidity distribution in the entire medical balloon catheter.

No limitation is placed on the material of tubes constituting the distal end shaft 10. When the distal end shaft 10 has a coaxial structure, polyolefins, polyolefin elastomers, polyesters, polyester elastomers, polyamides, polyamide elastomers, polyurethanes, polyurethane elastomers, and the like can be used for the inner tube 7. When the distal end shaft has a coaxial structure, because the guidewire lumen 4 is demarcated by the inner surface of the inner tube 7, from the standpoint of guidewire slidability it is preferred that polyethylene, in particular, high-density polyethylene, be used. The inner tube 7 can also have a multilayer structure, with the innermost layer being from high-density polyethylene and the outermost layer being from a material that can be adhesively bonded with or fused with the balloon 2. In order to improve further the guidewire slidability, a lubricating coating of silicone, Teflon, or the like can be provided on the inner surface of inner tube 7.

No limitation is placed on the material of outer tube 8. Thus, polyolefins, polyolefin elastomers, polyesters, polyester elastomers, polyamides, polyamide elastomers, polyurethanes, polyurethane elastomers, and the like, can be used.

Further, even when the distal end shaft 10 has a biaxial structure or any other structure, materials suitable for the above-described inner tube 7 or outer tube 8 can be used.

Resins such as polycarbonates, polyamides, polyurethanes, polysulfones, polyallylates, styrene-butadiene copolymers, polyolefins, and the like can be advantageously used as the material constituting the hub 3.

In order to improve visibility of balloon 2 under X ray imaging and to facilitate positioning of the balloon in the target zone of pathological changes, an X ray impermeable ring 9 may be provided on the outer surface of the distal end shaft present inside the balloon. The X ray impermeable ring 9 may be of any material with X ray impermeability, and metals or resins may be used for the ring. No limitation is also placed on the position and number of such rings and they can be set according to the target usage of the medical balloon catheter.

A hydrophilic coating can be provided on the outer surface of the medical balloon catheter to facilitate the insertion into blood vessels or guide catheter. Thus, a hydrophilic coating providing lubrication during contact with blood to zones which are in contact with blood is preferably provided on the outer surface of distal end shaft 10, outer surface of proximal end shaft 11, outer surface of balloon 2, and the like. No limitation is placed on the type of such hydrophilic coating, but hydrophilic polymers such as poly(2-hydroxyethyl methacrylate), polyacrylamide, polyvinyl pyrrolidone, or the like can be advantageously used. No limitation is placed on the coating method.

Depending on the target usage of the medical balloon catheter, a hydrophobic coating can be provided on the outer surface of balloon 2 in order to prevent slipping in the zone of pathological changes during inflation of balloon 2. No limitation is placed on the type of such hydrophobic coating. Hydrophobic polymers such as silicones can be advantageously used for the coating.

Figure 23:
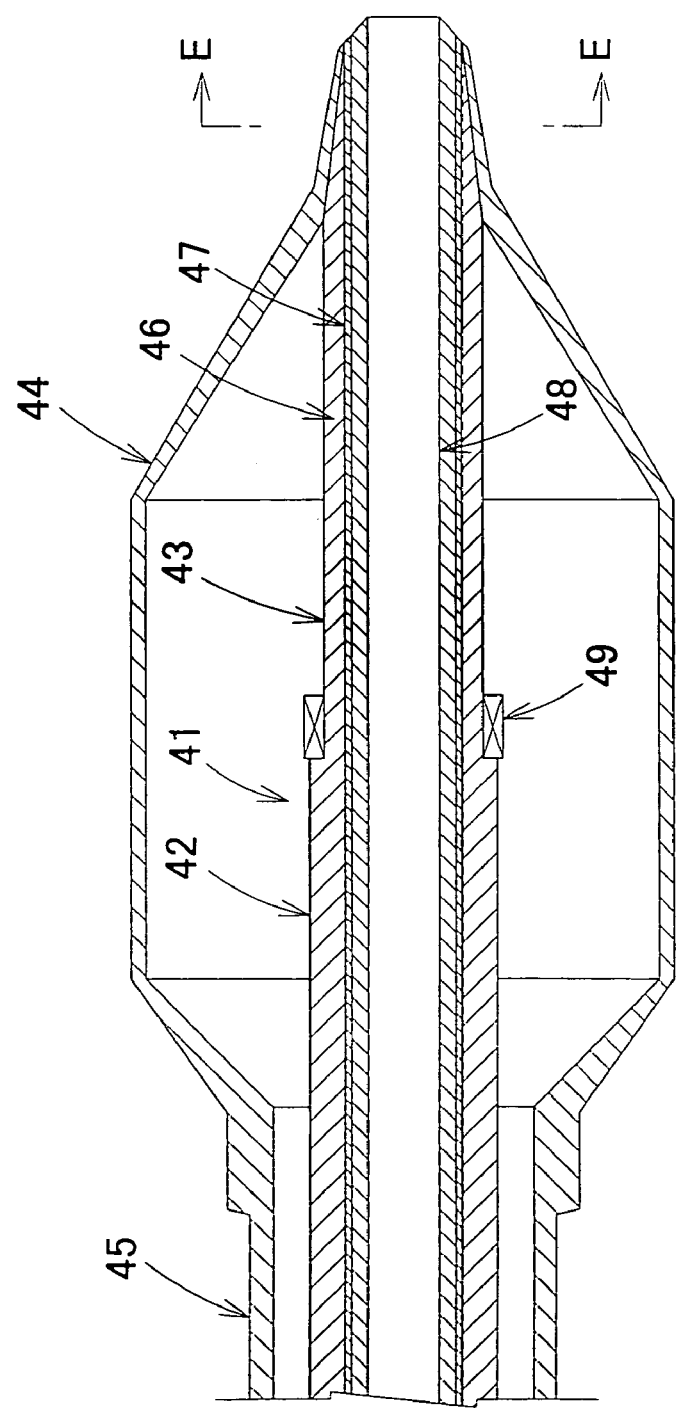
FIG. 23 is a cross-sectional schematic view illustrating the distal end portion of the balloon catheter containing a balloon and a tip portion of the balloon catheter in accordance with the present invention.
Figure 24:
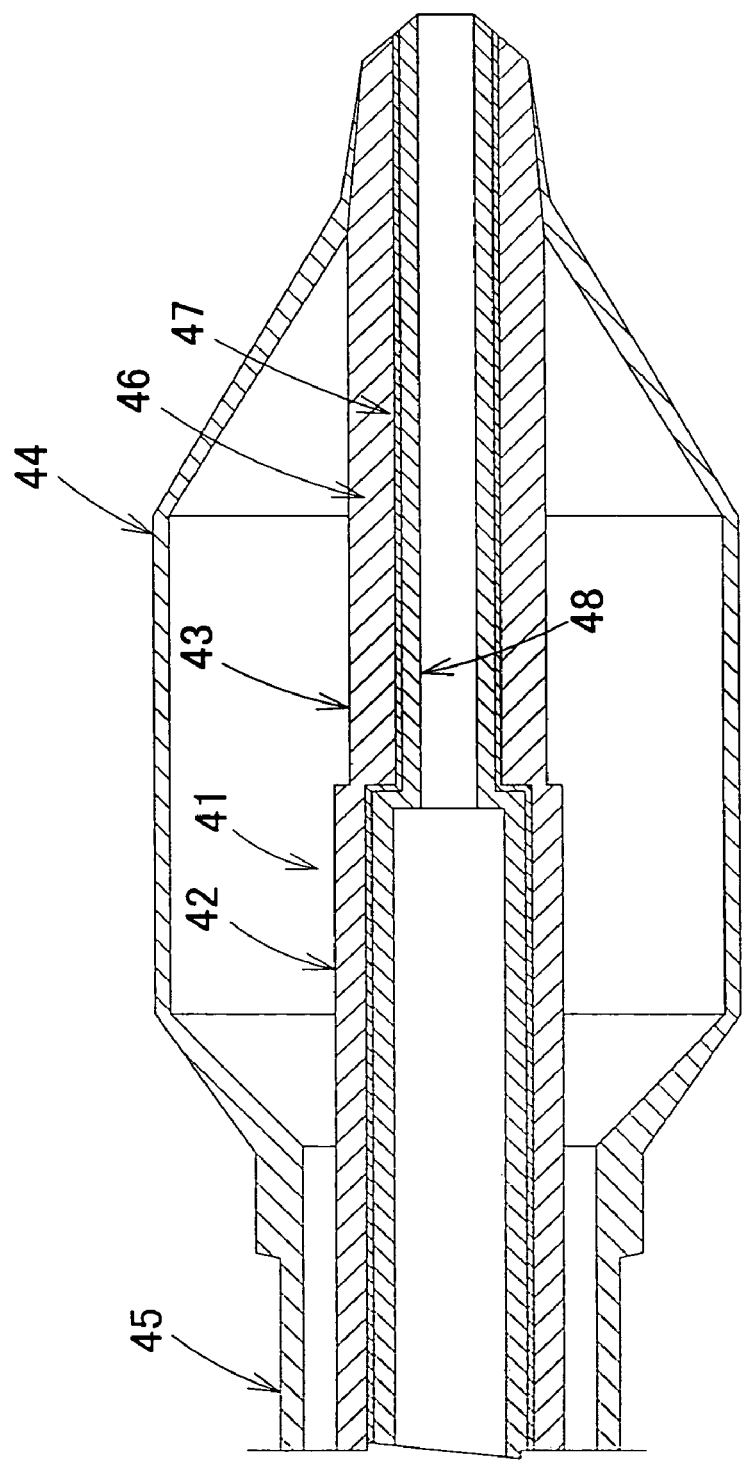
FIG. 24 is a cross-sectional schematic view illustrating the distal end portion of the balloon catheter containing a balloon and a tip port ion of the balloon catheter in accordance with the present invention.

An embodiment relating to the structure of the distal end portion including the balloon of the medical balloon catheter in accordance with the present invention will be explained below with reference to FIGS. 23 through 28, but the present invention is not limited thereto. The present invention relates to a balloon catheter composed of a plurality of tubes. FIGS. 23 and 24 illustrate an example in which the distal end portion comprises a balloon of the balloon catheter in accordance with the present invention, a tube having a lumen for passing a guidewire and formed so that the outer diameter on the distal end side is smaller than that on the proximal end side, and a tip portion.

Figure 26:
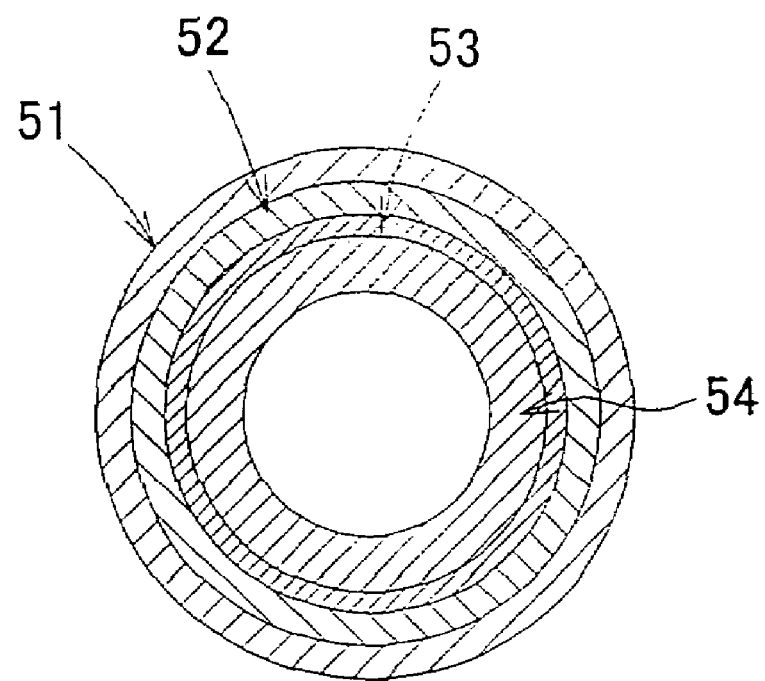
FIG. 26 is a cross-sectional view along the E-E' line in FIG. 23 and is a cross-sectional schematic view illustrating an example of the tip portion of the balloon catheter in accordance with the present invention.

Referring to FIG. 23, a tube 41 having a lumen for passing a guidewire is formed so that the outer diameter on the distal end portion 43 is smaller than that of the proximal end portion 42 and is arranged to pass inside the balloon 44. At the distalmost end of the catheter, the tube is coaxially fused, as shown in FIG. 26 (cross sectional view along the E-E' line in FIG. 23) to balloon 44, forming a tip portion. The balloon 44, on the other end thereof, is fused with a tube 45 constituting the outer surface of the catheter. The X ray impermeable ring 49 is designed so that the inner diameter thereof is larger than the outer diameter of the distal end portion 43 of tube 41 and smaller than the outer diameter of proximal end portion 42. The proximal end of X ray impermeable ring 49 is abutted onto and fixed to the boundary zone between the distal end portion and a small-diameter portion on the distal end side in tube 41. Referring to FIG. 24, the tube 41 having a lumen for passing a guidewire is formed so that the outer diameter of distal end portion 43 is less than the outer diameter of the proximal end portion 42 and that the inner diameter of distal end portion 43 is less than the inner diameter of distal end portion 42. Furthermore, tube 41 is arranged to pass inside the balloon 44, and at the distalmost end of the catheter, the tube is coaxially fused, as shown in FIG. 26 (cross sectional view along the E-E' line in FIG. 23) with balloon 44, forming a tip portion. On the other hand, the proximal end of balloon 44 is fused with a tube 45 constituting the outer surface of the catheter.

The inner diameter on the distal end side of tube 41 formed so that the outer diameter of distal end portion 43 is less than that of 42 may be equal to the inner diameter of proximal end portion, as shown in FIG. 23, or maybe less than the inner diameter of proximal end portion, as shown in FIG. 24.

Figure 25:
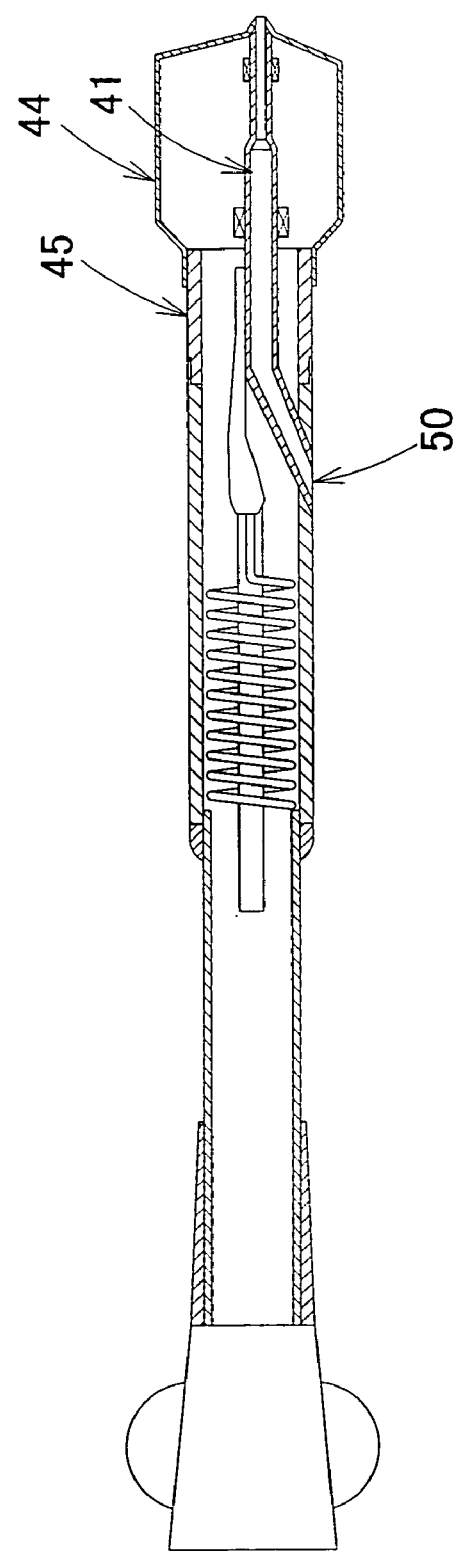
FIG. 25 is a cross-sectional schematic view illustrating the entire rapid exchange balloon catheter in accordance with the present invention.

FIG. 25 is a cross-sectional schematic view illustrating the entire rapid exchange balloon catheter in accordance with the present invention. The rapid exchange balloon catheter as referred to herein is typically a balloon catheter with a structure in which the tube 41 for passing a guidewire is made short in order to facilitate the exchange of the balloon catheter. The present invention is, however, not limited to the rapid exchange balloon catheters.

An embodiment of the present invention will be described below in greater detail. The present invention relates to a balloon catheter composed of a plurality of tubes and a balloon, this catheter having a structure in which the tube 41 formed to have an outer diameter on the distal end side smaller than that of the proximal end side and serving as the tube 41 for passing a guidewire inside thereof is arranged so as to pass inside the balloon and the balloon 44 and the small-diameter portion on the distal end side in the tube 41 are fused together in the vicinity of the distal end of the catheter, wherein the ratio of the outer diameter of the small-diameter portion on the distal end side in tube 41 to the outer diameter of the proximal end portion, (outer diameter of small-diameter portion on the distal end side)/(outer diameter of proximal end portion), is no less than 0.85. Because fusion is used for fixing the balloon 44 and tube 41, no adhesive layer is formed. As a result, the tip portion is provided with flexibility and discontinuity of flexibility therein can be reduced. Furthermore, from the standpoint of reducing the diameter and providing for continuity of flexibility, it is preferred that the ratio of the outer diameter of the small-diameter portion on the distal end side to the outer diameter of the proximal end portion, (outer diameter of small-diameter portion on the distal end side)/(outer diameter of proximal side portion), be no less than 0.85 and no more than 0.95. Thus, if the ratio less than 0.85, flexibility becomes discontinuous and an adverse effect can be produced. When the ratio is above 0.95, the degree of flexibility enhancement in the distal end of the catheter owing to diameter reduction is small. On the other hand, in addition to the structure shown in FIG. 23 and FIG. 24 in which a step is formed between the large-diameter section and a small-diameter section, a tapered structure with gradually changing diameter or a structure combining those two structures can be used. In this case, the diameter of tube 41 in the vicinity (in the position shifted by 5 mm from the fusion portion toward the proximal end) of the fusion portion with the distal end side of balloon 44 is used as the outer diameter of the small-diameter portion on the distal end side, and a diameter of tube 41 for passing a guidewire directly below the fusion portion (directly below the center of the fusion portion) of the proximal end side of balloon 44 and tube 45 constituting the outer surface of the catheter is used as the outer diameter of the proximal end portion. Further, from the standpoint of reducing the discontinuity of rigidity, the ratio of the thickness of the small-diameter portion on the distal end side and the thickness of the proximal end portion is preferably no less than 0.7, even more preferably, no less than 0.8.

Further, the present invention relates to a balloon catheter composed of a plurality of tubes and a balloon, this catheter having a structure in which the tube 41 formed to have an outer diameter on the distal end side smaller than that of the proximal end side and serving as the tube 41 for passing a guidewire inside thereof is arranged so as to pass inside the balloon and the balloon 44 and the small-diameter portion on the distal end side in the tube 41 are fused together in the vicinity of the distal end of the catheter, wherein any of the values of Shore hardness, or flexural modulus of elasticity, or melting point at least of that part of the small-diameter portion on the distal end side in the tube 41 which is fused with the balloon 44 are less that the respective values of the material constituting the balloon 44. Setting specific limitations on Shore hardness, flexural modulus of elasticity, and melting point makes it possible to improve further the flexibility of the guidewire tube itself, in addition to the effect obtained by forming a structure in which the ratio of the outer diameter of the small-diameter portion on the distal end side to the outer diameter of the portion on the proximal end side is no less than 0.85 and no more than 0.95, and to provide a balloon catheter with a more flexible distal end.

Further, the present invention provides a balloon catheter aimed at therapy of coronary artery and composed of a plurality of tubes and a balloon, this catheter having a structure in which the tube 41 formed to have an outer diameter on the distal end side smaller than that on the proximal end side and serving as the tube 41 for passing a guidewire inside thereof is arranged so as to pass inside the balloon 44 and the balloon 44 and the small-diameter portion on the distal end side in the tube 41 are fused together in the vicinity of the distal end of the catheter, wherein the outer diameter of the small-diameter portion on the distal end side in said tube is no more than 0.52 mm. As for the outer diameter of tube 41, in case of catheters for expanding a coronary artery, the outer diameter of no more than 0.52 mm and no less than 0.49 mm is preferred from the standpoint of strength required for the tube 41. Thus, if the outer diameter is above 0.52 mm, the degree of flexibility provided to the distal end of catheter is small, and if it is less than 0.49, the problem is associated with the decreased resistance of the tube to pressure.

Further, the balloon catheter in accordance with the present invention has a structure such that when the balloon 44 is composed of a polyester elastomer material or a polyamide elastomer material, at least that part of the small-diameter portion on the distal end side of guidewire tube 41 which is fused with the balloon 44 is formed of the resin of the same type as the balloon 44, that is from a polyester elastomer material or a polyamide elastomer material. As a result, fusion, which produces no adhesive layer, can be conducted. Therefore, the diameter of the tip portion can be decreased, flexibility can be improved, and discontinuity of flexibility can be reduced. Furthermore, in case of a structure in which the above-mentioned polyester elastomer materials or polyamide elastomer materials have hard segment and soft segment components in a molecule, employing a structure in which the ratio of soft segments in the material constituting the balloon 44 is less than the ratio of soft segments in the material constituting the tube 41 for passing a guidewire inside thereof makes it possible to provide a balloon catheter in which the flexibility of the tube 41 itself is increased and the flexibility of the distal end is increased.

No specific limitation is placed on the inner surface of guidewire tube 41, and a single-layer tube 41 may be made from the same material as the portion fused with the balloon 44, provided that a minimum required guidewire slidability is ensured. However, because materials with a low Shore hardness, flexural modulus, and melting point typically have poor sliding properties, it is preferred that a material with excellent sliding properties, which is different from that of the portion fused with the balloon 44, be arranged on the inner surface, and the innermost surface is preferably composed of high-density polyethylene. Furthermore, to enable fusion with the balloon 44, the portion of the guidewire tube 41, which is to be fused with the balloon 44, is preferably composed of a material with excellent fusibility with the balloon 44. Moreover, when the balloon 44 is composed of a polyester elastomer, the portion of tube 41 which is to be fused with the balloon 44 is preferably composed of a polyester elastomer, and when the balloon 44 is composed of a polyamide elastomer, the portion of tube 41 which is to be fused with the balloon 44 is preferably composed of a polyamide elastomer. The portion which is to be fused with balloon 44, as referred to herein, may be located anywhere, provided that it is a portion allowing the two members to be fixed by mixing with the material constituting the balloon during fusion and solidifying, but it is especially preferred that this portion be the outermost layer 46 of the tube 41. With the present structure, the guidewire tube 41 can be provided with a combination of fusion ability and high guidewire slidability. In this case, a layer of a material for providing the tube 41 with described mechanical properties, or a binder layer 47 may be present between the innermost layer and the portion which is to be fused with the balloon 44, no limitation being placed on the number, type, and thickness ratio of such layers. For example, when a binder layer 47 is formed, the conventional lamination technology and adhesive bonding technology can be applied. A safer balloon catheter in which interface peeling between the portion which is to be fused with the balloon 44 and the innermost surface 48 is made difficult can be provided if one or a plurality of materials having a solubility parameter (SP value) between those of the material layers constituting the portion which is to be fused with balloon 44 and the innermost surface 48 is arranged therebetween, or a material having adhesive properties is arranged on the portion which is to be fused with balloon 44 and the innermost surface. When the layer forming the portion which is to be fused with the balloon 44 is from a thermoplastic elastomer such as a polyester elastomer or a polyamide elastomer, it is preferred that the calculated flexural rigidity of the elastomer layer represented by a product of the tensile modulus of the elastomer and the geometrical moment of inertia determined by the dimensions and shape of the elastomer layer be controlled so as to be greater than that of the other layers. Further, as described above, the tube 41 represented in accordance with the present invention is often preferred to have a multilayer structure, and the tube 41 with the entirely multilayer structure can be used, but the tube in which only the small-diameter portion on the distal end side and vicinity thereof has a multilayer structure may be also used. Referring to FIG. 26, the reference symbol 51 stands for a material layer originating from balloon 44; 52—material layer originating from the outermost surface of guidewire tube 41; 53—material layer originating from the binder layer of guidewire tube 41; and 54—material layer originating from the innermost surface of guidewire tube 41. Since FIG. 26 is a cross-sectional view along the E-E' line in FIG. 23, reference signs 52, 53 and 54 of FIG. 26 correspond to reference signs 46, 47 and 48, respectively, of FIGS. 23 and 24.

Further, the present invention provides a balloon catheter aimed at therapy of coronary artery and composed of a plurality of tubes and a balloon, this catheter having a structure in which the tube 41 formed to have an outer diameter on the distal end side smaller than that on the proximal end side and serving as the tube 41 for passing a guidewire inside thereof is arranged so as to pass inside the balloon 44 and the balloon 44 and the small-diameter portion on the distal end side in the tube 41 are fused together in the vicinity of the distal end of the catheter, wherein that part of the small-diameter portion on the distal end side in the tube 41 which is to be fused with the balloon 44 is composed of a polyester elastomer having hard segments and soft segments in a molecule, and the ratio of soft segments is above 13%. From the standpoint of providing the distal end of catheter with flexibility, it is preferred that the ratio of soft segments of the polyester elastomer forming the part which is to be fused with balloon 44 be above 13%. The tip portion can be adjusted to a flexible condition by increasing flexibility inherent to guidewire tube 41 and by using fusion, which produces no adhesive layer, as a fixing method. On the other hand, it is preferred that the ratio of soft segments of the polyester elastomer forming the part which is to be fused with the balloon 44 be less than 70%, in order to prevent extreme deformation in response to pressure applied when the balloon 44 is inflated.

Further, the present invention provides a balloon catheter aimed at therapy of coronary artery and composed of a plurality of tubes and a balloon, this catheter having a structure in which the tube 41 formed to have an outer diameter on the distal end side smaller than that on the proximal end side and serving as the tube 41 for passing a guidewire inside thereof is arranged so as to pass inside the balloon 44 and the balloon 44 and the small-diameter portion on the distal end side in the tube 41 are fused together in the vicinity of the distal end of the catheter, wherein that part of the small-diameter portion on the distal end side in the tube 41 which is to be fused with the balloon 44 is composed of a polyamide elastomer having hard segments and soft segments in a molecule, and the ratio of soft segments is above 14%. From the standpoint of providing the distal end of catheter with flexibility, it is preferred that the ratio of soft segments of the polyamide elastomer forming the part which is to be fused with balloon 44 be above 14%. The tip portion can be adjusted to a flexible condition by increasing flexibility inherent to guidewire tube 41 and by using fusion, which produces no adhesive layer, as a fixing method. On the other hand, it is preferred that the ratio of soft segments of the polyamide elastomer forming the part which is to be fused with the balloon 44 be less than 70%, in order to prevent extreme deformation in response to pressure applied when the balloon 44 is inflated.

In the medical balloon catheter, the X ray impermeable ring 49 preferably is abutted against and fixed to the boundary portion of the proximal end side and the small-diameter portion on the distal end side of the guidewire tube 41. Thus, if the X ray impermeable ring 49 is arranged on the proximal end side which is thicker than the distal end portion 43, the flexibility of the portion where the ring is arranged will be further decreased by comparison with that on the distal end side. Moreover, because the X ray impermeable ring 49 is arranged so that it abuts against the boundary portion on the proximal end side, changes of flexibility from the thick proximal end side to the thin distal end side are smoothed and discontinuity of flexibility can be reduced.

Further, in accordance with the present invention, a structure may be also provided in which the tube 41 constituting the outer surface of the catheter is composed of a material fusible with the balloon 44 and fused with and arranged on the proximal end side of balloon 44. Employing a structure in which the tube 45 constituting the outer surface of the catheter is fused with the proximal end side of balloon 44 makes it possible to provide a medical balloon catheter which is flexible and in which discontinuity of flexibility hardly occurs on the proximal end side of balloon 44, because no new adhesive layer is formed.

Shore hardness indicated in the present invention can be measured by the method indicated in ASTM D 2240, flexural modulus of elasticity can be measured by the method indicated in ASTM D 790, and tensile modulus of elasticity can be measured by the method indicated in ASTM D 638. Melting point can be measured by using the conventional DSC measurement apparatus. The ratio of hard segments and soft segments in the materials indicated in the present invention is a weight ratio of components in the materials and can be measured by NMR.

EMBODIMENTS OF CATHETER SHAFT

The catheter shaft of the medical balloon catheter in accordance with the present invention will be described below in greater detail, based on specific embodiments and comparative examples thereof, but the present invention is not limited thereto.

Embodiment 1

A tubular parison (inner diameter 0.43 mm, outer diameter 0.89 mm) was fabricated by an extrusion molding method by using a polyamide elastomer (trade name: PEBAX7233SA01, manufactured by Elf Atochem Co.). Then, a balloon with an outer diameter of a straight tube portion of 3.0 mm was fabricated by a biaxial stretching and blowing method by using the parison.

The inner tube (inner diameter 0.42 mm, outer diameter 0.56 mm) and an outer tube (inner diameter 0.71 mm, outer diameter 0.88 mm) were fabricated by extrusion molding by using a polyamide elastomer (trade name: PEBAX7233SA01, manufactured by Elf Atochem Co.). The balloon and outer tube were joined by thermal fusion. Then, the inner tube and outer tube were arranged so as to obtain a coaxial double-wall tubular configuration and the balloon and inner tube were joined by thermal fusion. Notches with a length of half a perimeter in the circumferential direction were provided in part of the outer tube, the inner tube was thereafter fused in an exposed state to the outer surface of the outer tube, and a guidewire port was formed. The product was employed as a distal end shaft—balloon assembly. The outer surface of the balloon was coated with an aqueous solution of polyvinyl pyrrolidone.

A proximal end shaft (inner diameter 0.50 mm, outer diameter 0.66 mm) was fabricated from a stainless steel SUS316.

A spiral notch with a width of the spiral of 2 mm and a pitch of the spiral of 0.5 mm was formed by laser processing on a distal end portion with a length of 60 mm. The proximal end shaft and the distal end shaft—balloon assembly were arranged as shown in FIG. 7 and adhesively bonded with a two-liquid mixed-type urethane adhesive (trade name UR0531, manufactured by H. B. Fuller Co., Ltd.).

A hub was fabricated by an injection molding method using a polycarbonate (trade name Makloron 2658, manufactured by Bayer Co.). Once the hub and proximal end shaft have been adhesively joined with a two-liquid mixed-type urethane adhesive (trade name UR0531, manufactured by H. B. Fuller Co., Ltd.), the balloon was subjected to lapping and EOG sterilization treatment was conducted.

Embodiment 2

Fabrication was conducted in the same manner as in Embodiment 1, except that slits with a width of 0.3 mm and a spacing of 2 mm were provided with a length of half a perimeter in the circumferential direction by laser processing on a distal end portion (with a length of 50 mm) of a proximal end shaft, as shown in FIG. 12.

Embodiment 3

Fabrication was conducted in the same manner as in Embodiment 1, except that four round holes with a diameter of 0.4 mm were produced with equal spacing on the same circumference by laser processing on a distal end portion (with a length of 40 mm) of a proximal end shaft, the distance between the holes in the axial direction being 0.5 mm, as shown in FIG. 19.

Embodiment 4

The distal end portion of the proximal end shaft of Embodiment 1 was stretched to obtain a width of the spiral of 2 mm and a pitch of the spiral of 1.6 mm. Upon completion of stretching, fabrication was conducted in the same manner as in Embodiment 1, except that the distal end portion of the proximal end shaft was cut to a length of 60 mm.

Embodiment 5

Fabrication was conducted in the same manner as in Embodiment 1, except that, as shown in FIG. 20, the proximal end shaft was fabricated from a thermosetting polyimide, grooves with a width of 0.1 mm, a depth of 0.1 mm, and a spacing of 5 mm were produced by laser processing on a distal end portion (with a length of 70 mm) of a proximal end shaft, a core wire from stainless steel SUS 314 with a diameter of 0.25 mm was arranged from inside the proximal end shaft to the proximal end side of distal end shaft, and the core wire was adhesively bonded and secured to the outer peripheral surface of inner tube with a two-liquid mixed-type urethane adhesive (trade name UR0531, manufactured by H. B. Fuller Co., Ltd.).

COMPARATIVE EXAMPLE 1

Fabrication was conducted in the same manner as in Embodiment 1, except that no spiral notch of Embodiment 1 was provided in the distal end portion of proximal end shaft.

COMPARATIVE EXAMPLE 2

Fabrication was conducted in the same manner as in Embodiment 5, except that no groove of Embodiment 5 was provided in the distal end portion of proximal end shaft.

Embodiments 1 through 5 and Comparative Examples 1, 2 were evaluated by the following methods.

(Evaluation 1)

Figure 21:
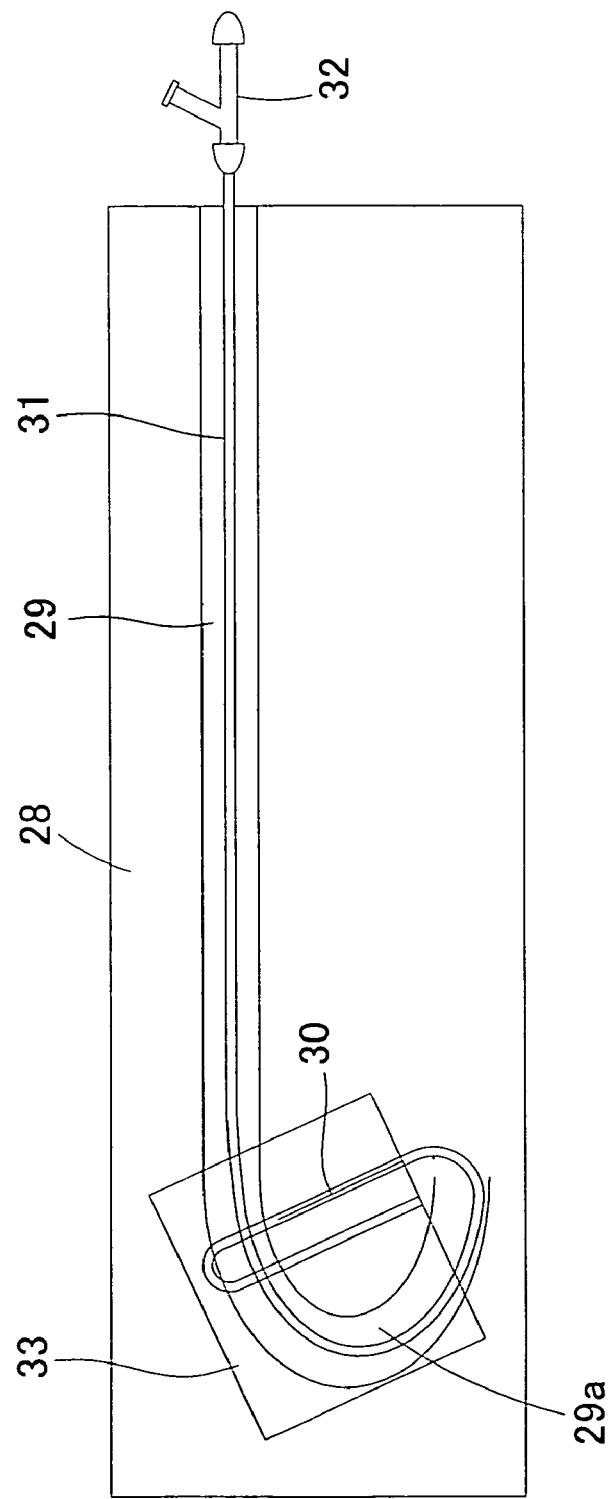
FIG. 21 is a schematic view illustrating a system for evaluating the medical balloon catheter.
Figure 22:
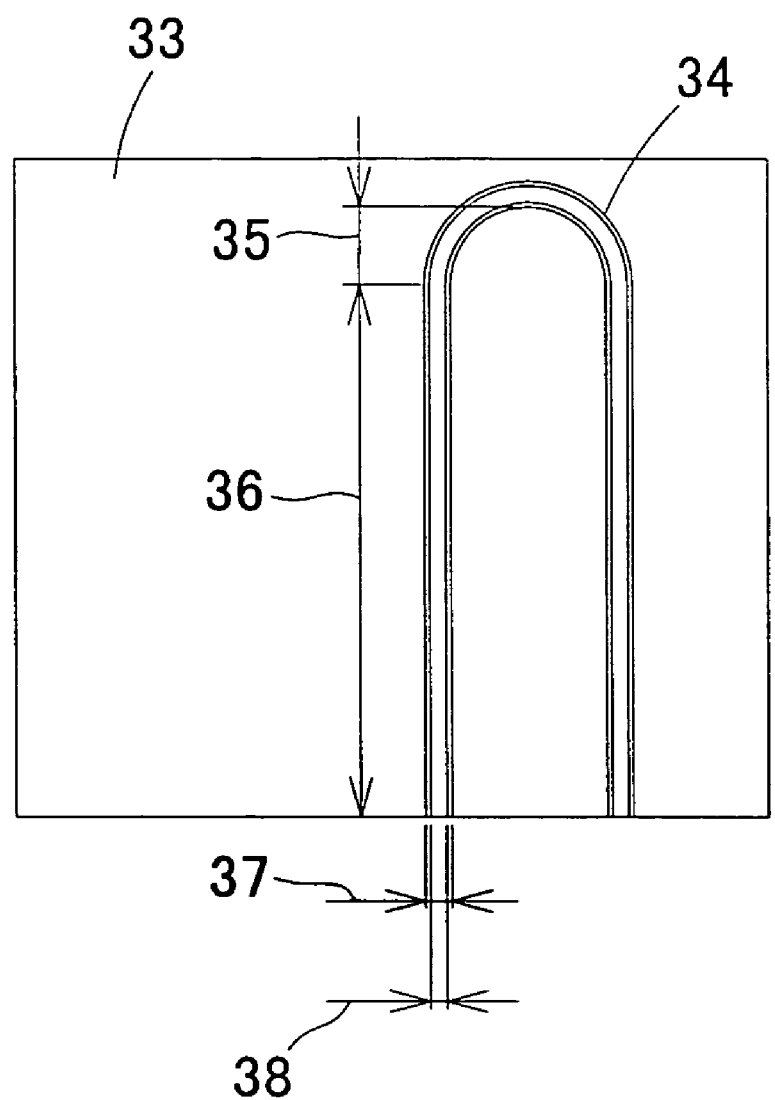
FIG. 22 is an expanded view of the curved plate shown in FIG. 21.

As shown in FIG. 21 and FIG. 22, an aorta model 29 and a guide catheter 31 were placed in a water tank 28 filled with a physiological solution at a temperature of 37° C., and a hemostat valve 32 was secured to the guide catheter. The distal end of guide catheter 31 was connected to a curved plate 33 simulating the coronary artery, and a guidewire 30 with a diameter of 0.014" (about 0.36 mm) was pre-inserted into the guide catheter 31. A polyethylene tube 34 was arranged in the curved plate 33. The polyethylene tube 34 was composed of a straight portion 36 and a curved portion 35. The length of the straight portion 36 was 80 mm, the curvature radius of the curved portion 35 was 15 mm, the outer diameter 37 of the polyethylene tube 34 was 5 mm, and the inner diameter 38 thereof was 3 mm. The far end of guidewire 30 was arranged at a distance of 50 mm from the far end of curved plate 33. The operation ability was evaluated when a medical balloon catheter was inserted from outside the water tank via the hemostat valve along the guidewire 30 located inside the guide catheter 31. The evaluation results are shown in Table 1.

(Evaluation 2)

Upon completion of Evaluation 1, the medical balloon catheter was pushed at a rate of 10 mm/sec to the far end portion of curved plate 33 connected to the distal end of guide catheter 31 by using a slide table, and a maximum generated load was measured with a digital force gage. The evaluation results are shown in Table 1.

Evaluation 1 was used to evaluate the kink resistance during insertion of the medical balloon catheter into a body from outside of the body. Evaluation 2 was mainly used to evaluate the trackability. Therefore, good results of both evaluations are the target effect of the present invention.

In Evaluation 1, good insertion operation ability was demonstrated in Embodiments 1 through 5 and kink formation was observed in none of the portions of the catheter shaft when it was passed through the hemostat valve.

On the other hand, in Comparative Examples 1, 2 a kink appeared in the catheter shaft in the distalmost portion of proximal end shaft when it passed through the hemostat valve. Kink formation could be prevented by conducting insertion at a very low speed, while grasping the distalmost portion of the proximal end shaft, but in such a case a large load was placed on the operator manipulating the medical balloon catheter and the operation ability could not be considered good.

In Evaluation 2, no kink appeared during passage through an aorta arc 29a or curved plate in Embodiments 1 through 5, a maximum load value was from 0.54 N to 0.71 N, and good trackability was demonstrated.

In Comparative Examples 1, 2 a kink appeared in the distalmost portion of proximal shaft when the distalmost portion of the proximal end shaft reached the vicinity of aorta arc 29a, and the medical balloon catheter was difficult to insert from the aorta arc to the distal end side. Therefore, trackability in Comparative Examples 1, 2 was considered to be very poor.

TABLE 1

Measurement results on kink resistance and trackability

|  | Evaluation 1 | Evaluation 2 |
| --- | --- | --- |
| Embodiment 1 | Good insertion operation ability, no kink appeared | Maximum generated load 0.65 N |
| Embodiment 2 | Good insertion operation ability, no kink appeared | Maximum generated load 0.60 N |
| Embodiment 3 | Good insertion operation ability, no kink appeared | Maximum generated load 0.71 N |
| Embodiment 4 | Good insertion operation ability, no kink appeared | Maximum generated load 0.54 N |
| Embodiment 5 | Good insertion operation ability, no kink appeared | Maximum generated load 0.59 N |
| Comparative Example 1 | Kink in the distal end portion of proximal end shaft | Kink in the distalmost portion of proximal end shaft in aorta arc |
| Comparative Example 2 | Kink in the distal end portion of proximal end shaft | Kink in the distalmost portion of proximal end shaft in aorta arc |

Embodiment of Distal End Portion of Catheter

More specific embodiments and comparative examples of the distal end portion of the medical balloon catheter in accordance with the present invention will be described below. The embodiments described below place no limitation on the present invention.

Embodiment 6

A rapid exchange balloon catheter for coronary artery with a distal end portion of the catheter shown in FIG. 2 was fabricated by passing a guidewire tube, in which the layer forming the outermost surface was composed of a polyester elastomer with a Shore hardness of 60D, a flexural modulus of elasticity of 274 MPa, a melting point of 216° C., and soft segment ratio of 22%, the innermost surface was composed of a high-density polyethylene, the outer diameter and inner diameter of the distal end portion were 0.50 mm and 0.40 mm, respectively, and the outer diameter and inner diameter of the proximal end portion were 0.56 mm and 0.42 mm, respectively, inside a balloon with a rated expansion value of 3.0 mm formed from a polyester elastomer with a Shore hardness of 72D, a flexural modulus of elasticity of 568 MPa, a melting point of 218° C., and a soft segment ratio of 13% and coaxially fusing the outer surface of the tube at the distal end of the distal end side of the balloon. The proximal end of the X ray impermeable ring was fixed in a position abutting against the boundary portion of the proximal end side and the small-diameter portion on the distal end side in the tube. Further, a polyester elastomer was used for the tube constituting the outer surface of the catheter, and the proximal end side of the balloon and the tube constituting the outer surface of the catheter were joined by fusion. The maximum diameter of the tip portion was 0.57 mm and the maximum diameter of the section from the tip portion to the balloon portion was 0.77 mm in the zone where the tapered portion of the balloon was folded in the vicinity of the boundary of the tip and balloon.

Embodiment 7

A rapid exchange balloon catheter for coronary artery with a distal end portion of the catheter shown in FIG. 24 was fabricated by passing a guidewire tube, in which the layer forming the outermost surface was composed of a polyamide elastomer with a Shore hardness of 55D, a flexural modulus of elasticity of 196 MPa, a melting point of 168° C., and a soft segment ratio of 35%, the innermost surface was composed of a high-density polyethylene, the outer diameter and inner diameter of the distal end portion were 0.51 mm and 0.39 mm, respectively, and the outer diameter and inner diameter of the proximal end portion were 0.56 mm and 0.42 mm, respectively, inside a balloon with a rated expansion value of 3.0 mm formed from a polyamide elastomer with a Shore hardness of 70D, a flexural modulus of elasticity of 430 MPa, a melting point of 172° C., and a soft segment ratio of 14% and coaxially fusing the outer surface of the tube at the distal end of the distal end side of the balloon. The proximal end of the X ray impermeable ring was fixed in a position abutting against the boundary portion of the proximal end side and the small-diameter portion on the distal end side in the tube. Further, a polyamide elastomer was used for the tube constituting the outer surface of the catheter, and the proximal end side of the balloon and the tube constituting the outer surface of the catheter were joined by fusion. The maximum diameter of the tip portion was 0.56 mm and the maximum diameter of the section from the tip portion to the balloon portion was 0.77 mm in the zone where the tapered portion of the balloon was folded in the vicinity of the boundary of the tip and balloon.

COMPARATIVE EXAMPLE 3

A rapid exchange balloon catheter for coronary artery was fabricated by passing a tube for passing a guidewire, in which the layer forming the outermost surface was composed of a polyester elastomer with a Shore hardness of 60D, a flexural modulus of elasticity of 274 MPa, a melting point of 216° C., and a soft segment ratio of 22%, the innermost surface was composed of a high-density polyethylene, and the outer diameter and inner were 0.56 mm and 0.42 mm, respectively, inside a balloon with a rated expansion value of 3.0 mm formed from a polyester elastomer with a Shore hardness of 72D, a flexural modulus of elasticity of 568 MPa, a melting point of 218° C., and a soft segment ratio of 13% and coaxially fusing the outer surface of the tube at the distal end of the distal end side of the balloon. Further, a polyester elastomer was used for the tube constituting the outer surface of the catheter, and the proximal end side of the balloon and the tube constituting the outer surface of the catheter were joined by fusion. The maximum diameter of the tip portion was 0.63 mm and the maximum diameter of the section from the tip portion to the balloon portion was 0.83 mm in the zone where the tapered portion of the balloon was folded in the vicinity of the boundary of the tip and balloon.

COMPARATIVE EXAMPLE 4

A rapid exchange balloon catheter for coronary artery was fabricated by passing a tube for passing a guidewire, in which the layer forming the outermost surface was composed of a polyamide elastomer with a Shore hardness of 55D, a flexural modulus of elasticity of 196 MPa, a melting point of 168° C., and a soft segment ratio of 35%, the innermost surface was composed of a high-density polyethylene, and the outer diameter and inner diameter were 0.56 mm and 0.42 mm, respectively, inside a balloon with a rated expansion value of 3.0 mm formed from a polyamide elastomer with a Shore hardness of 70D, a flexural modulus of elasticity of 430 MPa, a melting point of 172° C., and a soft segment ratio of 14% and coaxially fusing the outer surface of the tube at the distal end of the distal end side of the balloon. Further, a polyamide elastomer was used for the tube constituting the outer surface of the catheter, and the proximal end side of the balloon and the tube constituting the outer surface of the catheter were joined by fusion. The maximum diameter of the tip portion was 0.62 mm and the maximum diameter of the section from the tip portion to the balloon portion was 0.85 mm in the zone where the tapered portion of the balloon was folded in the vicinity of the boundary of the tip and balloon.

COMPARATIVE EXAMPLE 5

A rapid exchange balloon catheter for coronary artery was fabricated by passing a tube for passing a guidewire, in which the layer forming the outermost surface was composed of a polyester elastomer with a Shore hardness of 72D, a flexural modulus of elasticity of 568 MPa, a melting point of 218° C., and a soft segment ratio of 13%, the innermost surface was composed of a high-density polyethylene, and the outer diameter and inner were 0.56 mm and 0.42 mm, respectively, inside a balloon with a rated expansion value of 3.0 mm formed from a polyester elastomer with a Shore hardness of 72D, a flexural modulus of elasticity of 568 MPa, a melting point of 218° C., and a soft segment ratio of 13% and coaxially fusing the outer surface of the tube at the distal end of the distal end side of the balloon. Further, a polyester elastomer was used for the tube constituting the outer surface of the catheter, and the proximal end side of the balloon and the tube constituting the outer surface of the catheter were joined by fusion. The maximum diameter of the tip portion was 0.63 mm and the maximum diameter of the section from the tip portion to the balloon portion was 0.85 mm in the zone where the tapered portion of the balloon was folded in the vicinity of the boundary of the tip and balloon.

COMPARATIVE EXAMPLE 6

A rapid exchange balloon catheter for coronary artery was fabricated by passing a tube for passing a guidewire, in which the layer forming the outermost surface was composed of a polyamide elastomer with a Shore hardness of 70D, a flexural modulus of elasticity of 430 MPa, a melting point of 172° C., and a soft segment ratio of 14%, the innermost surface was composed of a high-density polyethylene, and the outer diameter and inner diameter were 0.56 mm and 0.42 mm, respectively, inside a balloon with a rated expansion value of 3.0 mm formed from a polyamide elastomer with a Shore hardness of 70D, a flexural modulus of elasticity of 430 MPa, a melting point of 172° C., and a soft segment ratio of 14% and coaxially fusing the outer surface of the tube at the distal end of the distal end side of the balloon. Further, a polyamide elastomer was used for the tube constituting the outer surface of the catheter, and the proximal end side of the balloon and the tube constituting the outer surface of the catheter were joined by fusion. The maximum diameter of the tip portion was 0.63 mm and the maximum diameter of the section from the tip portion to the balloon portion was 0.85 mm in the zone where the tapered portion of the balloon was folded in the vicinity of the boundary of the tip and balloon.

COMPARATIVE EXAMPLE 7

A commercial rapid exchange balloon catheter for coronary artery with a rated expansion value of 3.0 mm was used that was manufactured by passing a tube for passing a guidewire, in which the layer forming the outermost surface was composed of a polyamide with a melting point of 178° C. and the innermost surface was composed of a high-density polyethylene, inside a balloon formed from a polyamide with a melting point of 178° C. and coaxially fusing the outer surface of the tube at the distal end of the distal end side of the balloon. Further, a polyamide elastomer was used for the tube constituting the outer surface of the catheter, and the proximal end side of the balloon and the tube constituting the outer surface of the catheter were joined by fusion. The maximum diameter of the tip portion was 0.78 mm and the maximum diameter of the section from the tip portion to the balloon portion was 0.89 mm in the zone where the tapered portion of the balloon was folded in the vicinity of the boundary of the tip and balloon.

COMPARATIVE EXAMPLE 8

A commercial rapid exchange balloon catheter for coronary artery with a rated expansion value of 3.0 mm was used that was manufactured by passing a tube for passing a guidewire, which was composed of a polyamide with a melting point of 176° C. and a soft segment ratio of 7%, inside a balloon formed from a polyamide with a melting point of 173° C. and a soft segment ratio of 17% and coaxially fusing the outer surface of the tube at the distal end of the distal end side of the balloon. Further, a polyamide elastomer was used for the tube constituting the outer surface of the catheter, and the proximal end side of the balloon and the tube constituting the outer surface of the catheter were joined by fusion. The maximum diameter of the tip portion was 0.64 mm and the maximum diameter of the section from the tip portion to the balloon portion was 0.82 mm in the zone where the tapered portion of the balloon was folded in the vicinity of the boundary of the tip and balloon.

Characteristics of guidewire tubes and balloons of various types used in the above-described Embodiments 3, 4 and Comparative Examples 3 through 8 are presented in Table 2 and Table 3, respectively.

TABLE 3

Characteristics of balloons used in embodiments and comparative examples

| Units | Rated expansion value of balloon mm | Material | Shore hardness — | Flexural modulus of elasticity MPa | Melting point ° C. | Ratio of soft segments % |
|---|---|---|---|---|---|---|
| B1 | 3.0 | TPEE | 72D | 568 | 218 | 13 |
| B2 | 3.0 | TPAE | 70D | 430 | 172 | 14 |
| B3 | 3.0 | PA | | | 178 | 0 |
| B4 | 3.0 | TPAE | | | 173 | 17 |

Note:
TPEE: polyester elastomer
TPAE: polyamide elastomer
PA: polyamide (Evaluation)

Comparison of tip portions of Embodiments 6, 7, which are the balloon catheters in accordance with the present invention, with any of tip portions of Comparative Examples 3, 4, 5, 6, 7, and 8 demonstrates that the tip portions of the embodiments have a smaller maximum diameter within a range from the tip to the balloon portion and are more flexible. Further, discontinuity of flexibility in Embodiments 6 and 7 did not seem to be large.

Figure 27:
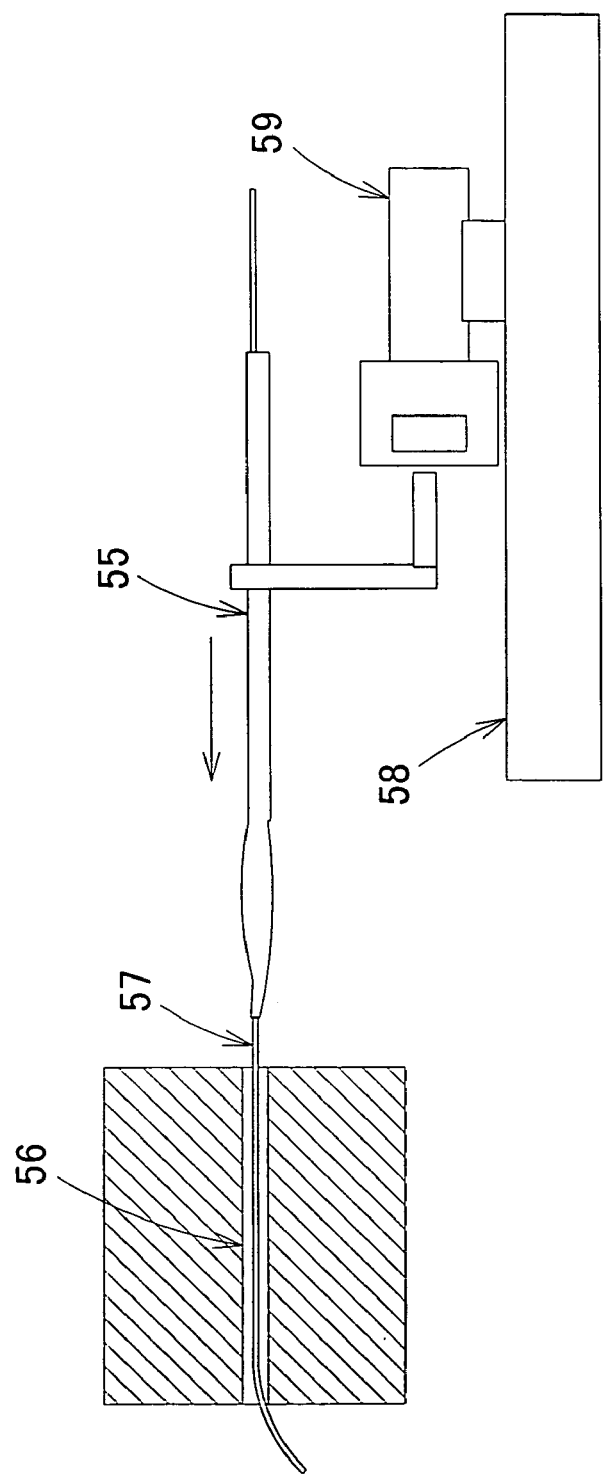
FIG. 27 illustrates schematically a measurement system used for Evaluation 3 employed for demonstrating the effect of the present invention.

The balloon catheters of Embodiments 6, 7 and Comparative Examples, 3, 4, 5, 6, 7, and 8 were tested by passing a balloon catheter 55 along a guidewire 57 at a constant rate in the evaluation system (Evaluation 3) shown schematically in FIG. 27, that is, in a constricted channel 56 in the model through which the guidewire 57 has been passed, and a load that was applied to the balloon catheter when the balloon passed through the constricted portion from the tip was measured. The inner diameter of the constricted portion in the constricted channel 56 inside the model was 0.65 mm and the channel was molded from a silicone with a Shore hardness of 40 D. The measurement was conducted in a state

TABLE 2

Characteristics of tubes for passing a guidewire that were used in embodiments and comparative examples

| Units | Material of outermost layer | Material of innermost layer | Shore hardness of material of outer-most layer — | Flexural modulus of material of outer-most layer MPa | Melting point of material of outer-most layer ° C. | Ratio of soft segments in material of outer-most layer % | Diameter of distal end side Outer diam., mm | Diameter of distal end side Inner diam., mm | Diameter of proximal end side Outer diam., mm | Diameter of proximal end side Inner diam., mm |
|---|---|---|---|---|---|---|---|---|---|---|
| GT1 | TPEE | HDPE | 60D | 274 | 216 | 22 | 0.50 | 0.40 | 0.56 | 0.42 |
| GT2 | TPAE | HDPE | 55D | 196 | 168 | 35 | 0.51 | 0.39 | 0.56 | 0.42 |
| GT3 | TPEE | HDPE | 60D | 274 | 216 | 22 | 0.56 | 0.42 | 0.56 | 0.42 |
| GT4 | TPAE | HDPE | 55D | 196 | 168 | 35 | 0.56 | 0.42 | 0.56 | 0.42 |
| GT5 | TPEE | HDPE | 72D | 568 | 218 | 13 | 0.56 | 0.42 | 0.56 | 0.42 |
| GT6 | TPAE | HDPE | 70D | 430 | 172 | 14 | 0.56 | 0.42 | 0.56 | 0.42 |
| GT7 | PA | HDPE | | | 178 | 0 | | | | |
| GT8 | TPAE | TPAE | | | 176 | 7 | | | | |

Note:
TPEE: polyester elastomer
TPAE: polyamide elastomer
PA: polyamide
HDPE: high-density polyethylene in which the balloon of the balloon catheter was folded on the periphery of guidewire tube.

Figure 28:
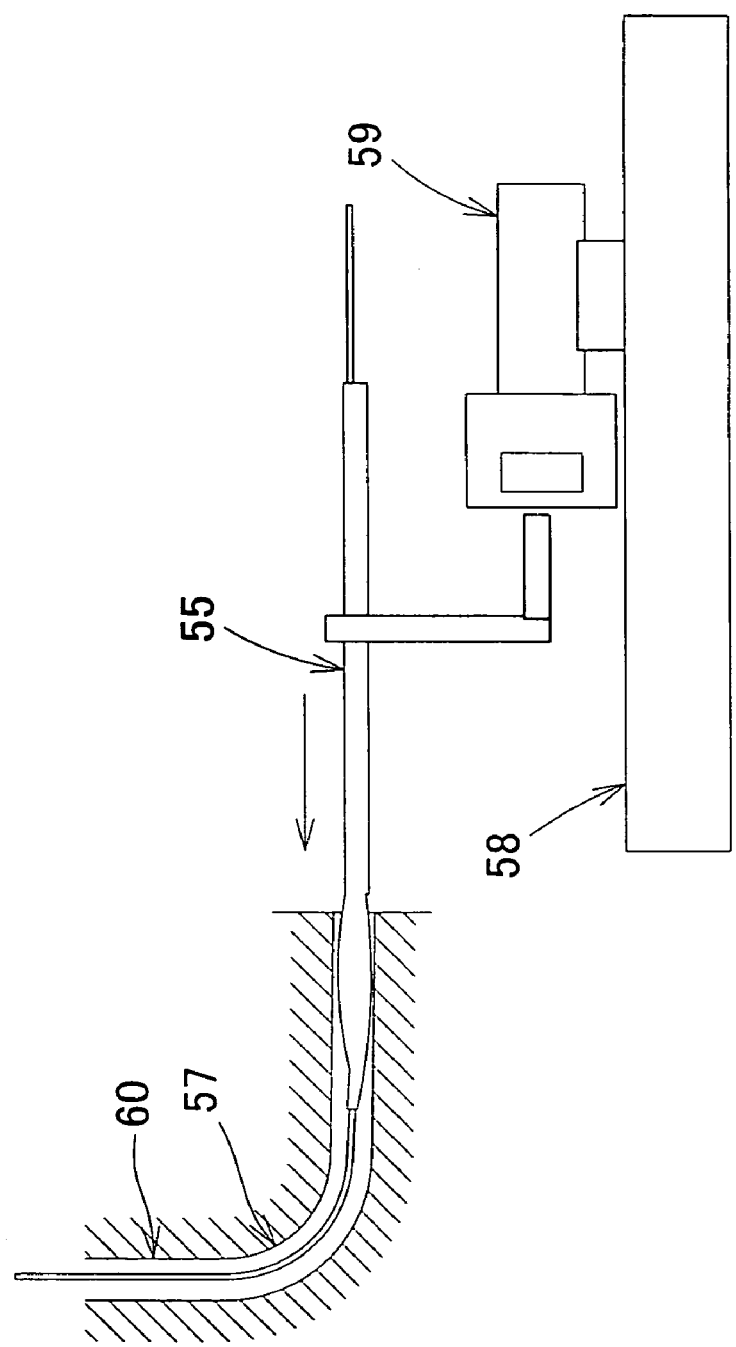
FIG. 28 illustrates schematically a measurement system used for Evaluation 4 employed for demonstrating the effect of the present invention.

The balloon catheters of Embodiments 6, 7 and Comparative Examples, 3, 4, 5, 6, 7, and 8 were also tested by passing a balloon catheter 55 along a guidewire 57 at a constant rate in the evaluation system (Evaluation 4) shown schematically in FIG. 28, that is, in a curved channel 60 in a model body fabricated from a polyethylene tube with an inner diameter of 1.5 mm that was curved at 90 degrees and had a curvature of 5 mm. The channel had a guidewire 57 arranged inside thereof and physiological solution with a temperature adjusted to 37. degree. C. was circulated therein. In the test, a load that was applied to the balloon catheter 55 when the tip portion passed through the curved portion was measured. The inner surface of the polyethylene tube serving as the curved channel 60 inside the model body was coated with a hydrophilic coating to prevent the effect of the surface state of the balloon catheter.

The results of Evaluation 3 and Evaluation 4 are presented in Table 4. The results show that the balloon catheters of Embodiments 6, 7 in accordance with the present invention could be passed into the constricted channel 56 in the model body with a load lower than that required in comparative example, had a small diameter of the zone from the tip portion to the balloon portion, and had excellent operation ability. Those results also show that in the balloon catheters of the embodiments, the balloon catheter tip portions could be passed through the curved channel 60 in the model body with a load lower than that required in comparative example, the tip portion were flexible, and the catheters had excellent operation ability.

TABLE 4

Structures of embodiments and comparative examples and the results obtained with measurement systems of Evaluations 3 and 4

| | Structure of catheter distal end portion | | Measurement results | |
|---|---|---|---|---|
| | Guidewire tube | Balloon | Evaluation 3 Load peak (N) | Evaluation 4 Load peak (N) |
| Embodiment 6 | GT1 | B1 | 0.355 | 0.085 |
| Embodiment 7 | GT2 | B2 | 0.310 | 0.077 |
| Comparative Example 3 | GT3 | B1 | 0.638 | 0.118 |
| Comparative Example 4 | GT4 | B2 | 0.688 | 0.098 |
| Comparative Example 5 | GT5 | B1 | 0.690 | 0.333 |
| Comparative Example 6 | GT6 | B2 | 0.689 | 0.314 |
| Comparative Example 7 | GT7 | B3 | 1.095 | 0.343 |
| Comparative Example 8 | GT8 | B4 | 0.657 | 0.265 |

Note:
GT1 - 8 correspond to Table 2,
B1 - 4 correspond to Table 3.

INDUSTRIAL APPLICABILITY

In accordance with the present invention, a medical balloon catheter can be readily provided in which the rigidity of catheter shaft is caused to change continuously in the longitudinal direction of the catheter shaft and pushability and kink resistance are increased, while the profile of a catheter shaft is being held to a minimum and crossability and trackability are being maintained.

Further, with the present invention, a medical balloon catheter can be obtained in which the zone from the tip to the balloon is thin, the flexibility of the tip portion is high and discontinuity of flexibility is small, this medical balloon catheter having excellent operation ability, in particular, the ability to penetrate into highly constricted zones of pathological changes, highly curved zones of pathological changes, and very hard zones of pathological changes.

The invention claimed is:

1. A medical balloon catheter composed of a plurality of tubes and a balloon, this catheter having a structure in which a tube formed to have an outer diameter on a distal end side is consistently smaller along the entire length thereof than that on a proximal end side and serving as a tube for passing a guidewire inside thereof is arranged so as to pass inside the balloon and the balloon and the small-diameter portion on the distal end side in said tube are fused together in the vicinity of the distal end of the catheter, wherein a ratio of the outer diameter of the small-diameter portion on the distal end side in said tube to the outer diameter of the proximal end portion, (outer diameter of the small-diameter portion on the distal end side)/(outer diameter of the proximal end portion), is no less than 0.85, wherein the outer diameter of the small-diameter portion on the distal end side in said tube is no more than 0.52 mm, wherein a proximal end of an X ray impermeable ring is abutted against and permanently fixed to the boundary portion of the proximal end side and the small-diameter portion on the distal end side of the tube for passing a guidewire inside thereof, wherein a tube constituting the outer surface of the catheter is composed of a material that can be fused with the balloon and is fused and arranged on the proximal end side of the balloon.

2. A medical balloon catheter composed of a plurality of tubes and a balloon, this catheter having a structure in which a tube formed to have an outer diameter on a distal end side is consistently smaller along the entire length thereof than that on a proximal end side and serving as a tube for passing a guidewire inside thereof is arranged so as to pass inside the balloon and the balloon and the small-diameter portion on the distal end side in said tube are fused together in the vicinity of the distal end of the catheter, wherein a Shore hardness of the material constituting at least that part of the small-diameter portion on the distal end side in said tube which is fused to the balloon is less than the Shore hardness of the material constituting the balloon, wherein a ratio of the outer diameter of the small-diameter portion on the distal end side in said tube to the outer diameter of the proximal end portion, (outer diameter of the small-diameter portion on the distal end side)/(outer diameter of the proximal end portion), is no less than 0.85, wherein the outer diameter of the small-diameter portion on the distal end side in said tube is no more than 0.52 mm, wherein a proximal end of an X ray impermeable ring is abutted against and permanently fixed to the boundary portion of the proximal end side and the small-diameter portion on the distal end side of the tube for passing a guidewire inside thereof, wherein a tube constituting the outer surface of the catheter is composed of a material that can be fused with the balloon and is fused and arranged on the proximal end side of the balloon.

3. A medical balloon catheter composed of a plurality of tubes and a balloon, this catheter having a structure in which a tube formed to have an outer diameter on a distal end side is consistently smaller along the entire length thereof than that on a proximal end side and serving as a tube for passing a guidewire inside thereof is arranged so as to pass inside the balloon and the balloon and the small-diameter portion on the distal end side in said tube are fused together in the vicinity of the distal end of the catheter, wherein a flexural modulus of elasticity of the material constituting at least that part of the small-diameter portion on the distal end side in said tube which is fused to the balloon is less than the flexural modulus of elasticity of the material constituting the balloon, wherein a ratio of the outer diameter of the small-diameter portion on the distal end side in said tube to the outer diameter of the proximal end portion, (outer diameter of the small-diameter portion on the distal end side)/(outer diameter of the proximal end portion), is no less than 0.85, wherein the outer diameter of the small-diameter portion on the distal end side in said tube is no more than 0.52 mm, wherein a proximal end of an X ray impermeable ring is abutted against and permanently fixed to the boundary portion of the proximal end side and the small-diameter portion on the distal end side of the tube for passing a guidewire inside thereof, wherein a tube constituting the outer surface of the catheter is composed of a material that can be fused with the balloon and is fused and arranged on the proximal end side of the balloon.

4. A medical balloon catheter composed of a plurality of tubes and a balloon, this catheter having a structure in which a tube formed to have an outer diameter on a distal end side is consistently smaller along the entire length thereof than that on a proximal end side and serving as a tube for passing a guidewire inside thereof is arranged so as to pass inside the balloon and the balloon and the small-diameter portion on the distal end side in said tube are fused together in the vicinity of the distal end of the catheter, wherein a melting point of the material constituting at least that part of the small-diameter portion on the distal end side in said tube which is fused to the balloon is lower than the melting point of elasticity of the material constituting the balloon, wherein a ratio of the outer diameter of the small-diameter portion on the distal end side in said tube to the outer diameter of the proximal end portion, (outer diameter of the small-diameter portion on the distal end side)/(outer diameter of the proximal end portion), is no less than 0.85, wherein the outer diameter of the small-diameter portion on the distal end side in said tube is no more than 0.52 mm, wherein a proximal end of an X ray impermeable ring is abutted against and permanently fixed to the boundary portion of the proximal end side and the small-diameter portion on the distal end side of a tube for passing a guidewire inside thereof, wherein the tube constituting the outer surface of the catheter is composed of a material that can be fused with the balloon and is fused and arranged on the proximal end side of the balloon.

5. A medical balloon catheter composed of a plurality of tubes and a balloon, this catheter having a structure in which a tube formed to have an outer diameter on a distal end side is consistently smaller along the entire length thereof than that on a proximal end side and serving as a tube for passing a guidewire inside thereof is arranged so as to pass inside the balloon and the balloon and the small-diameter portion on the distal end side in said tube are fused together in the vicinity of the distal end of the catheter, wherein a part of the small-diameter portion on the distal end side in said tube which is fused to the balloon is composed of a polyester elastomer having hard segments and soft segments in a molecule and a ratio of the soft segments is higher than 13%, wherein a ratio of the outer diameter of the small-diameter portion on the distal end side in said tube to the outer diameter of the proximal end portion, (outer diameter of the small-diameter portion on the distal end side)/(outer diameter of the proximal end portion), is no less than 0.85, wherein the outer diameter of the small-diameter portion on the distal end side in said tube is no more than 0.52 mm, wherein a proximal end of an X ray impermeable ring is abutted against and permanently fixed to the boundary portion of the proximal end side and the small-diameter portion on the distal end side of a tube for passing a guidewire inside thereof, wherein the tube constituting the outer surface of the catheter is composed of a material that can be fused with the balloon and is fused and arranged on the proximal end side of the balloon.

6. A medical balloon catheter composed of a plurality of tubes and a balloon, this catheter having a structure in which a tube formed to have an outer diameter on a distal end side is consistently smaller along the entire length thereof than that on a proximal end side and serving as a tube for passing a guidewire inside thereof is arranged so as to pass inside the balloon and the balloon and the small-diameter portion on the distal end side in said tube are fused together in the vicinity of the distal end of the catheter, wherein a part of the small-diameter portion on the distal end side in said tube which is fused to the balloon is composed of a polyamide elastomer having hard segments and soft segments in a molecule and a ratio of the soft segments is higher than 14%, wherein a ratio of the outer diameter of the small-diameter portion on the distal end side in said tube to the outer diameter of the proximal end portion, (outer diameter of the small-diameter portion on the distal end side)/(outer diameter of the proximal end portion), is no less than 0.85, wherein the outer diameter of the small-diameter portion on the distal end side in said tube is no more than 0.52 mm, wherein a proximal end of an X ray impermeable ring is abutted against and permanently fixed to the boundary portion of the proximal end side and the small-diameter portion on the distal end side of a tube for passing a guidewire inside thereof, wherein the tube constituting the outer surface of the catheter is composed of a material that can be fused with the balloon and is fused and arranged on the proximal end side of the balloon.

* * * * *